United States Patent [19]

Kamen

[11] Patent Number: 5,682,901

[45] Date of Patent: Nov. 4, 1997

[54] METHOD AND APPARATUS FOR MEASURING AUTONOMIC ACTIVITY OF A PATIENT

[76] Inventor: Peter Walter Kamen, 106 Thames Street, Box Hill,, Victoria, Australia, 3128

[21] Appl. No.: 581,582

[22] PCT Filed: Aug. 3, 1994

[86] PCT No.: PCT/AU94/00442

§ 371 Date: Jan. 16, 1996

§ 102(e) Date: Jan. 16, 1996

[87] PCT Pub. No.: WO95/03739

PCT Pub. Date: Feb. 9, 1995

[30] Foreign Application Priority Data

Aug. 3, 1993 [AU] Australia .......................... PM0301/93

[51] Int. Cl.⁶ .......................................... A61B 5/0456
[52] U.S. Cl. .......................................... 128/706; 128/708
[58] Field of Search ................ 364/413.06; 128/696, 128/702, 705, 710, 706, 708; 607/5

[56] References Cited

U.S. PATENT DOCUMENTS 5,201,321  4/1993  Fulton ................................ 128/702
5,447,520  9/1995  Spano et al. ........................ 128/705

OTHER PUBLICATIONS

Woo et al, "Patterns of Beat-to-Beat Heart Rate Variability in Advanced Heart Failure", American Heart Journal, vol. 123, 1992, pp. 704–710.

Bigger et al, "Comparison of time-and Frequency Domain-Based Measures of Cardiac Parasympathetic Activity in Holter Recordings After Myocardial Infarction", The American Journal of Cardiology, 1989, vol. 64, pp. 536–538.

Goldberger, "Nonlinear Dynamics, Fractals and Chaos: Applications to Cardiac Electrophysiology", Annals of Biomedical Engineering, 1990, vol. 18, pp. 195–198.

Denton et al, "Fascinating Rhythm: A Primer on Chaos Theory and Its Application to Cardiology", American Heart Journal, 1990, vol. 120, pp. 1419–1440.

Grassberger et al, "Measuring the Strangeness of Strange Attractors", Physica 9D, 1983, pp. 189–208.

Grassberger, "Generalized Dimensions of Strange Attractors", Physics Letters, 1983, vol. 97A, No. 6, pp. 227–230.

Skinner et al, "Correlation Dimension of Heartbeat Intervals is Reduced in Conscious Pigs by Myocardial Ischemia", Circulation Research, 1991, vol. 68, No. 4, pp. 966–976.

Woo et al, "Heart Rate Variability in Congenial Central Hypoventilation Syndrome", Pediatric Research, 1992, vol. 31, No. 3, pp. 291–296.

Raetz et al, "Dynamic Characteristics of Cardia R-R Intervals During Sleep and Waking States", Sleep, 1991, vol. 14, No. 6, pp. 526–533.

Malpas et al, "Heart Rate Variability and Cardiac Autonomic Function in Men with Chronic Alcoholic Dependence", BR Heart J, 1991, vol. 65, pp. 84–88.

(List continued on next page.)

*Primary Examiner*—Scott M. Getzow

[57] ABSTRACT

A method and apparatus for measuring activity of the autonomic nervous system of a patient involves obtaining ECG signals form the patient while the patient is at rest, measuring the R-R intervals for adjacent PQRS portions of the signals and generating a Poincaré plot from the R-R intervals. The ECG signals are obtained for a period of less than one hour, and from the Poincaré plot a determination can be made as to whether the autonomic activity represented by the plot can be used to quantify a degree of heart failure in the patient. The level of sympathetic activity of the patient can be quantified by determining a correlation dimension corresponding to the plot, and then a degree of heart failure in the patient determined on the basis of the correlation dimension when it lies outside a predetermined range. Furthermore, the level of parasympathetic activity for the patient can also be quantified by reference to the width of the plot about a line perpendicular to the line of identity of the plot.

19 Claims, 25 Drawing Sheets

OTHER PUBLICATIONS

Malpas et al, "Circadian Variation of Heart Rate Variability", Cardiovascular Research, 1990, vol. 24, pp. 210–213.

Malpas et al, "Heart Rate Variability During Hypoglycaemia", Diabetic Medicine, 1989, vol. 6, pp. 822–823.

Osaka et al, "Correlation Dimension of Heart Rate Variability: a New Index of Human Autonomic Function", Frontiers Med. Biol. Engng., 1993, vol. 5, No. pp. 289–300.

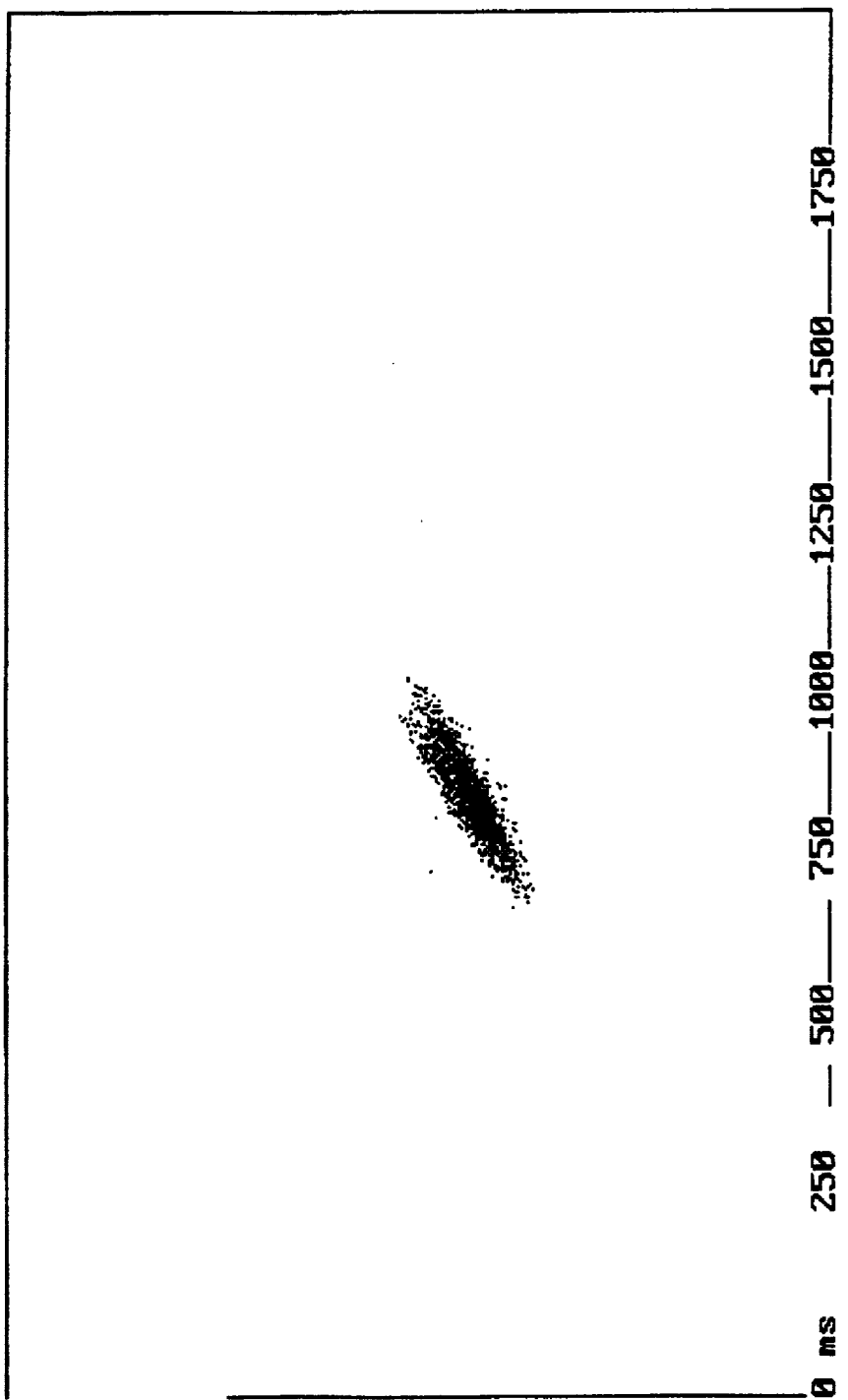

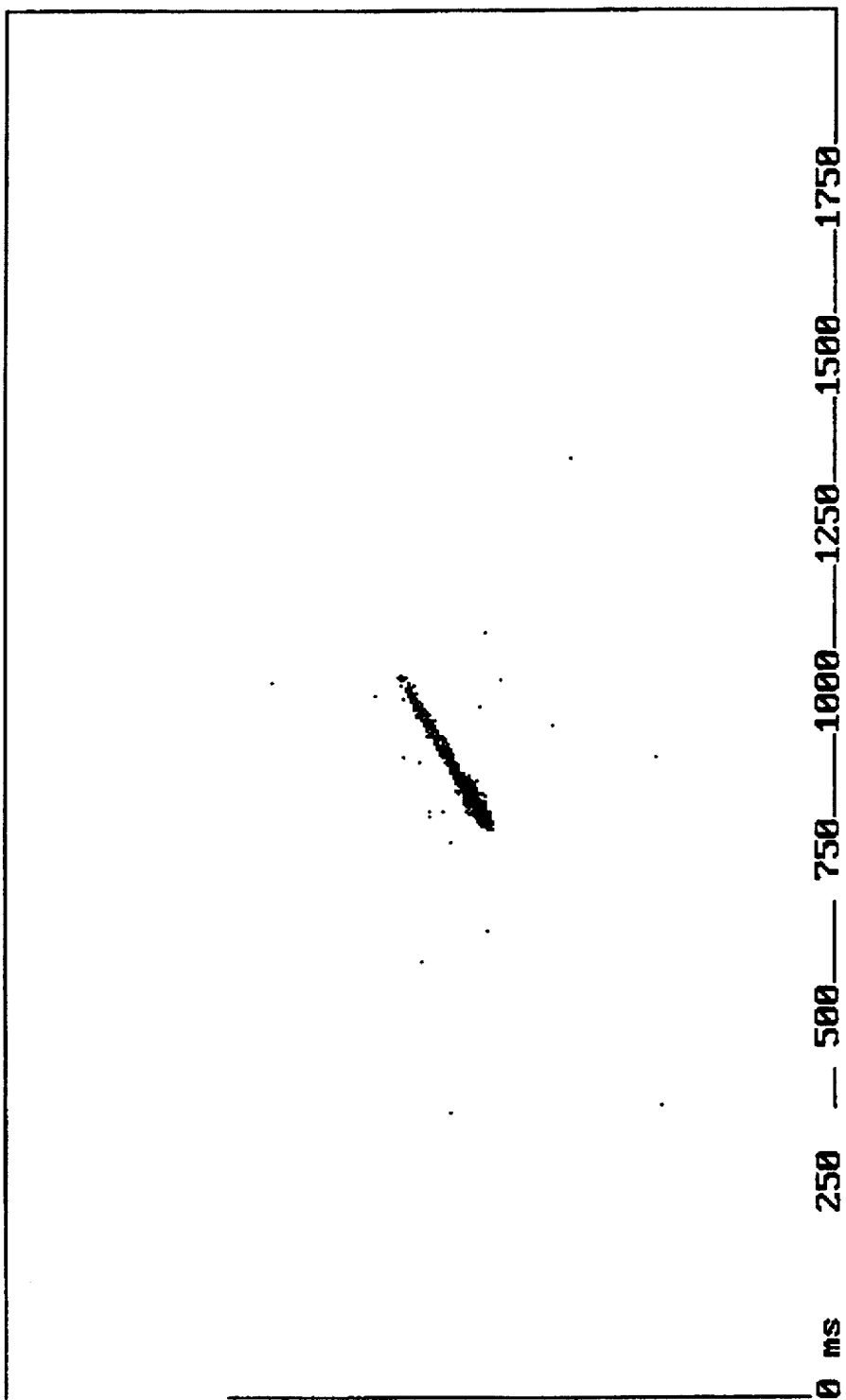

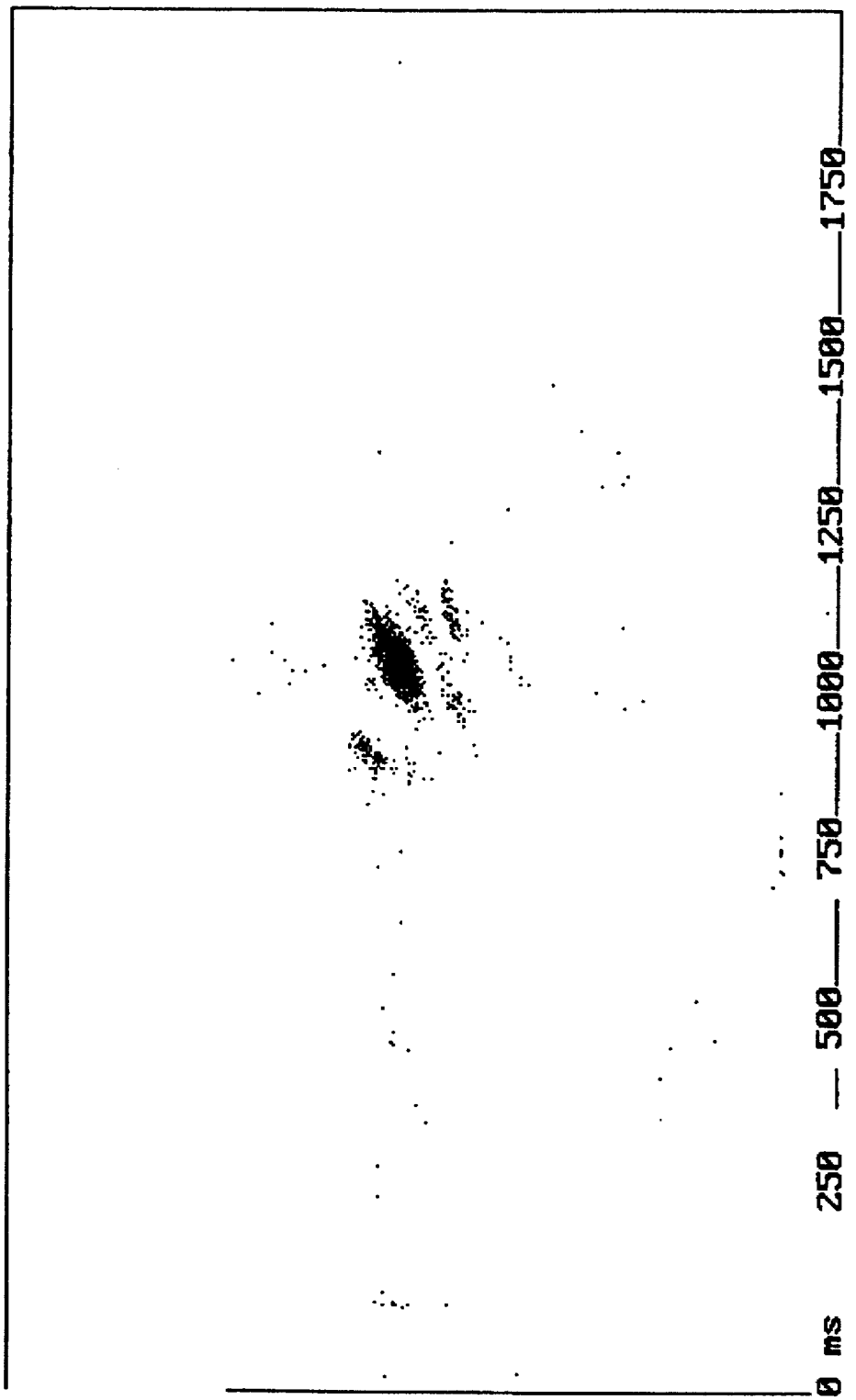

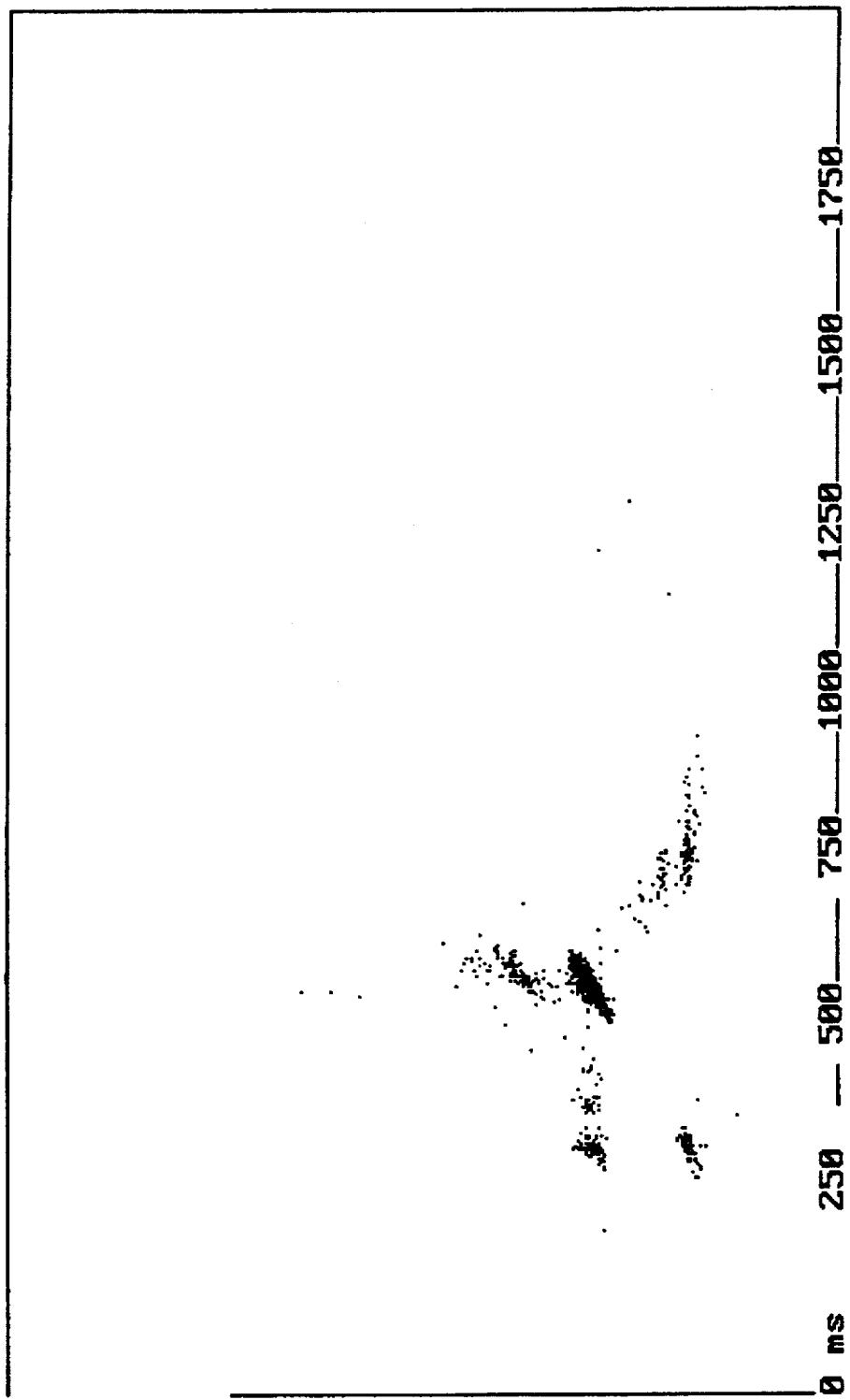

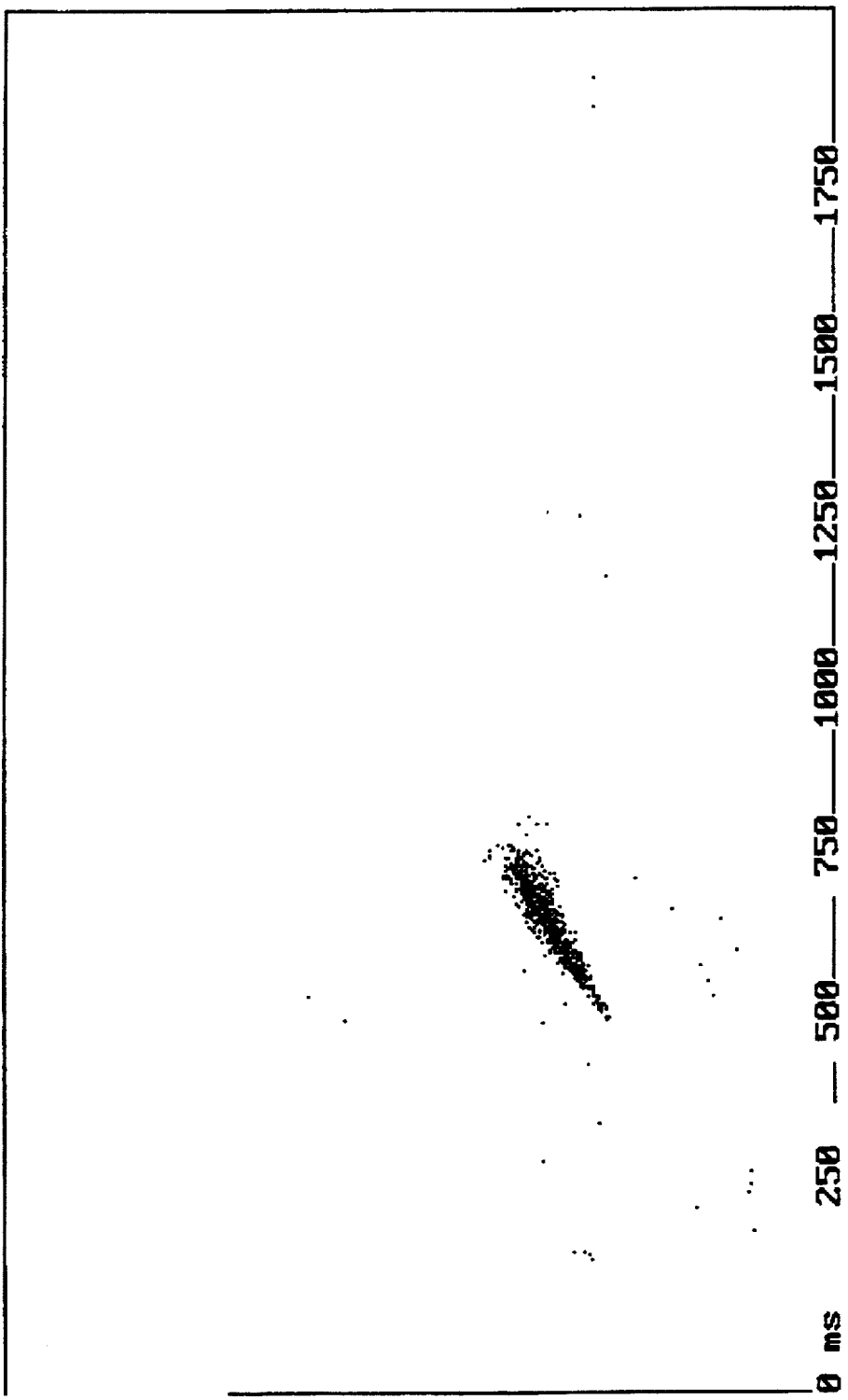

METHOD AND APPARATUS FOR MEASURING AUTONOMIC ACTIVITY OF A PATIENT

BACKGROUND OF THE INVENTION

1. Field of the Invention

The present invention relates to a method of measuring autonomic activity of a patient and a method of determining a level or degree of heart failure in a patient.

2. Related Art

The rate at which a human heart beats is controlled by a feedback loop provided by a neurohumoral mechanism, the basic component of which is the autonomic nervous system, i.e. the sympathetic and parasympathetic nervous system. The autonomic nervous system is believed to modulate the natural activity of the sinus node of the heart. The sinus node effectively provides a contraction signal for the chambers of the heart, which is further modulated by the atrioventricular (A/V) node which controls movement of the ventricles. The frequency of the sinus node increases when sympathetic activity increases and decreases with increased parasympathetic activity. The resulting instantaneous heart rate provides quantitative information on the activity of the system.

Increased sympathetic and depressed parasympathetic nervous activity is common in heart failure. Acute myocardial ischaemia can be accompanied by signs of either sympathetic or parasympathetic hyperactivity. A number of experimental and clinical studies have shown that sympathetic system activity and reactivity is increased in an important subgroup of hypertensive patients. Increased sympathetic activity is suspected of predisposing the heart to ventricular fibrillation.

Heart rate variability can be decreased with severe ischaemic heart disease, congestive heart failure, ageing and diabetic neuropathy. The sympathetic nervous system, the renin-angiotensin system, and arginine vasopressin may represent potential and real targets for pharmacologic manipulation. The early identification of patients with severe ischaemic heart disease and severe heart failure at high risk of sudden death is a prerequisite for early aggressive intervention.

Furthermore, with the improvement in recent years of surgical and medical management, the accurate determination and classification of patients into high and low risk groups is becoming increasingly important. Therefore a method and apparatus for measuring autonomic activity and accurately detecting and determining the level or degree of heart failure in a patient is particularly desirable.

A number of heart rate variability studies have been conducted in the past and relied on the conventional understanding that the heart constitutes a linear system. For example, the standard deviation of the period between consecutive heart beats of a patient has been used in the past to determine whether the patient is susceptible to hem rate variability and increased sympathetic activity. However, this measure has been found to be in valid in particular cases and is extremely sensitive to artefact and ectopic activity. A group of American doctors has recently applied non-linear analysis techniques to analyse heart rate variability. The doctors attached Holter monitors to a number of healthy and heart failure risk patients over 24 hour periods and the recorded signals were analysed to extract R-R interval data of each patient. Electronic signals representative of the human heart beat have a characteristic PQRS shape waveform for each beat, and the R-R interval is the period of time between successive R peaks of adjacent waveforms. Poincaré plots, as discussed hereinafter, were produced from the obtained R-R interval data but could not be used to accurately determine heart failure or the degree of heart failure, as the variability was open to influence by a number of external factors during the 24 hour period, and consequently was dependent on activities conducted by the subjects.

BRIEF SUMMARY OF THE INVENTION

In accordance with the present invention there is provided a method of measuring activity of the autonomic nervous system of a patient comprising:

obtaining EGG signals from said patient whilst said patient is at rest;

measuring the R-R intervals for adjacent PQRS portions of said signals; and generating a Poincaré plot from said R-R intervals.

Advantageously, the method includes determining a level of parasympathetic activity for said patient from the width of said plot about a line perpendicular to the line of identity of said plot.

The present invention further provides a method of determining a level of heart failure in a patient comprising:

obtaining ECG signals from said patient whilst said patient is at rest;

measuring the R-R intervals for adjacent PQRS portions of said signals; and generating and displaying a Poincaré plot of said R-R intervals from which a level of autonomic activity can be determined which corresponds to a level of heart failure.

The present invention also provides a method of quantifying a degree of heart failure in a patient comprising:

obtaining ECG signals from said patient whilst said patient is at rest;

measuring the R-R intervals for adjacent PQRS portions of said signals; and processing said R-R intervals to determine a correlation dimension of a chaotic attractor, wherein a Poincaré plot of said R-R intervals represents a Poincaré section of said attractor, and quantifying a degree of heart failure in said patient if said correlation dimension lies outside a predetermined range.

The present invention further provides a method of quantifying a degree of heart failure in a patient comprising:

obtaining ECG signals from said patient whilst said patient is at rest;

measuring the R-R intervals for adjacent PQRS portions of said signals;

generating and displaying a Poincaré plot of said R-R intervals;

determining a level of parasympathetic activity for said patient from the width of said plot about a line perpendicular to the line of identity of said plot;

determining the standard deviation of $\Delta$R-R intervals; and quantifying a degree of heart failure of said patient on the basis of said width and said standard deviation.

The present invention provides an apparatus for measuring activity of the autonomic nervous system of a patient, comprising:

means for obtaining ECG signals from said patient whilst said patient is at rest;

means for measuring the R-R intervals for adjacent PQRS portions of said signals;

means for generating a Poincaré plot from said R-R intervals; and means for determining the level of autonomic activity of the patient represented by the plot.

Advantageously, the apparatus may include means for determining a level of parasympathetic activity for said patient from the width of said plot about a line perpendicular to the line of identity of said plot.

The present invention also provides an apparatus for determining a level of heart failure in a patient comprising:

means for obtaining ECG signals from said patient whilst said patient is at rest;

means for measuring the R-R intervals for adjacent PQRS portions of said signals; and means for generating and displaying a Poincaré plot of said R-R intervals from which a level of autonomic activity corresponding to a level of heart failure can be determined.

The present invention also provides an apparatus for quantifying a degree of heart failure in a patient comprising:

means for obtaining ECG signals from said patient whilst said patient is at rest;

means for measuring the R-R intervals for adjacent PQRS portions of said signals;

means for processing said R-R intervals to determine a correlation dimension of a chaotic attractor, wherein a Poincaré plot of said R-R intervals represents a Poincaré section of said attractor; and means for quantifying a degree of heart failure in said patient if said correlation dimension lies outside a predetermined range.

The present invention further provides an apparatus for quantifying a degree of heart failure in a patient comprising:

means for obtaining ECG signals from said patient whilst said patient is at rest;

means for measuring the R-R intervals for adjacent PQRS portions of said signals;

means for generating and displaying a Poincaré plot of said R-R intervals from which heart failure can be determined;

means for determining a level of parasympathetic activity for said patient from the width of said plot about a line perpendicular to the line of identity of said plot;

means for determining the standard deviation of ΔR-R intervals; and means for quantifying a degree of heart failure of said patient on the basis of said width and said standard deviation.

BRIEF DESCRIPTION OF THE DRAWINGS

Preferred embodiments of the present invention are hereinafter described, by way of example only, with reference to the accompanying drawings, wherein:

FIGS. 4A, 4B and 4C are cluster Poincaré plots produced by the apparatus;

FIGS. 6A and 6B are cigar or torpedo Poincaré plots produced by the apparatus;

FIGS. 8A, 8B and 8C are complex pattern Poincaré plots produced by the apparatus;

FIG. 9A, 9B and 9C is a comet shape Poincaré plot produced by the apparatus;

DETAILED DESCRIPTION OF EXEMPLARY EMBODIMENTS

Figure 1:
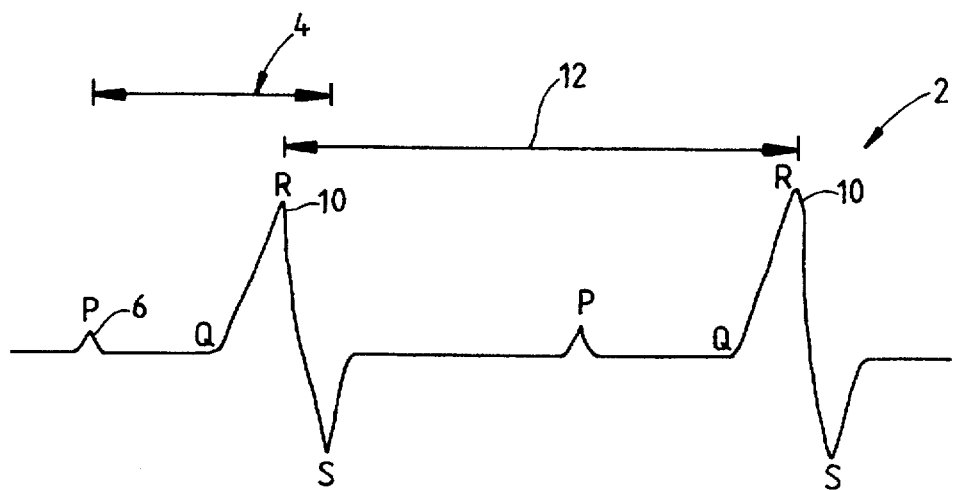
FIG. 1 is an example of an ECG signal waveform.

The electrocardiograph (ECG) signal 2 produced by an ECG machine which is representative of a person's heart beat has a characteristic PQRS portion 4 for each beat, as shown in FIG. 1. The P peak 6 corresponds to atrial contraction of the heart and the R peak 10 corresponds to contraction of the ventricles. The time between adjacent PQRS portions of an ECG signal 2 is a measure of a persons heart rate and the time between consecutive R peaks 10, known as the R-R interval 12, is normally used as a basis for heart rate studies because the R peaks 10 are relatively easy to detect compared to the remaining PQS segments of the characteristic portion 4.

Figure 2:
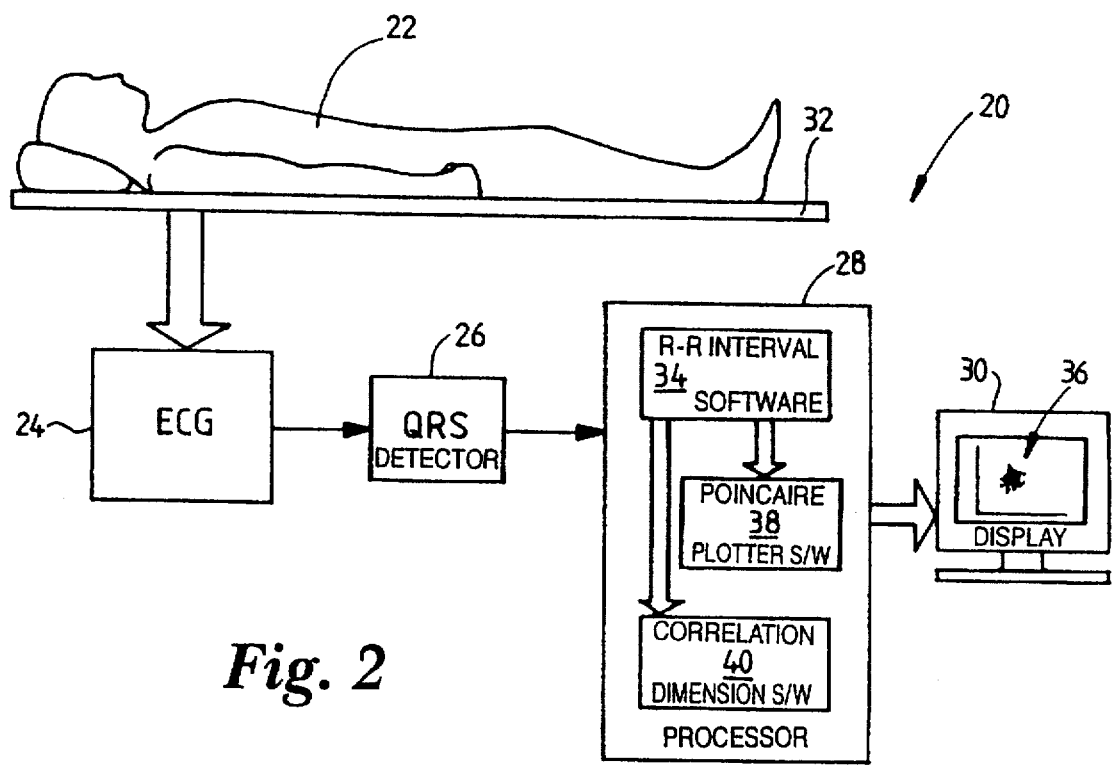
FIG. 2 is a block diagram of a preferred embodiment of an apparatus according to the present invention.

An apparatus 20 for measuring activity of the sympathetic and parasympathetic system of a patient 22, as shown in FIG. 2, includes a 12 lead ECG machine 24, such as the Burdick Elite, a QRS detector 26, and a processing system 28 having a visual display monitor 30. The patient 22 is placed in a stationary position at rest on a table 32 and connected to the ECG machine 24. The output of the ECG machine 24 is connected to the input of the QRS detector 26. The detector 26 detects the R peaks 10 of the signals 2 generated by the ECG machine 24 and inputs a voltage pulse to the processing system 28 for each detected R peak. The processing system 28, which may be an IBM™ 486 Personal Computer, includes an R-R interval program 34 which polls for the pulses from the QRS detector 26 and records the time between received pulses in a data file for the patient 22. A listing of the program is provided at the end of this specification. The patient dam file therefore comprises a list of recorded R-R intervals. The QRS detector 26 comprises a peak detector and a voltage comparator which is calibrated to an accuracy of ±1 ms. A number of different techniques may be used to obtain the R-R interval data file for a patient. For example, the QRS detector 26 may be replaced by an analogue/digital converter and the R-R interval program 34 modified to accept the data generated by the converter and determine the time between adjacent R peaks from the data. Another alternative, which has been found particularly advantageous, is for the QRS detector 26 to include a differential amplifier to detect the P, peaks, a counter and a 4 MHz oscillator. The amplifier on detecting the rising edge of an R peak 10 resets the counter, which counts cycles of the oscillator. The amplifier also causes the previous count to be read by the processing system 28. The R-R interval program 34 converts each cycle count to time, and a listing of the program appears at the end of this specification.

Once the R-R interval data file for the patient 22 has been completed after monitoring the patient 22 for a predetermined period of time, for example 30 minutes, a Poincaré plot 36 of the R-R intervals of the data file is produced on the monitor 30 using a Poincaré plot program 38 of the processing system 28. A listing of a plot program 38 is provided at the end of this specification and, in conjunction with the R-R interval program 34 also produces a Poincaré plot as the intervals are determined and recorded. The Poincaré plot is based on the principle of mathematically slicing across the trajectory of a dynamical system on a plane in the system in order to isolate a section of the system so as to simplify its analysis. The instantaneous R-R intervals held in the data file may be considered to represent a person's heart beat at the instant time when the cardiac dynamical process crosses an imaginary plane. The Poincaré plot 36 is a scatter plot of current R-R interval plotted against the previous R-R interval, i.e. $R-R_{n-1}$ vs. $R-R_n$. The plot corresponds to the imaginary plane, and the points of the plot represent the points at which the cardiac process crosses the plane. If there is minimal variation in the R-R intervals, then the plot will include a characteristic centre cluster of points, however, if there is considerable variation in the R-R intervals, then the points of the plot will be relatively diffuse. FIGS. 3 to 11, as discussed hereinafter, illustrate the variety of Poincaré plots 36 which can be obtained. The Poincaré plot advantageously displays heart rate variability information in a compact, easily interpreted form which can be used to determine the level of heart failure and complement other standard procedures in the analysis of heart rate variability, such as R-R interval histograms, tachograms and standard deviation.

Chaotic oscillations are induced in biological membranes such as cardiac cells, molluscan neurons, pacemaker neurons and squid giant axons. I believe that the sinus node can be considered to be a collection of oscillators entrained electrotonically that comprise a chaotic oscillator subject to non-linear forcing of the neurohumoral axis of the heart by the autonomic nervous system. This is contrary to conventional theory which, in particular, suggests the heart is subject to linear control by the neurohumoral mechanism. A chaotic process is that one appears disorganised but is actually deterministic provided appropriate mathematical tools are used. The variabilities in R-R intervals are not random but exhibit short range correlations that are governed by deterministic laws and these correlations are related to accelerating and decelerating physiological processes. A mathematical object, known as an attractor, may be used to represent a dynamical system, and a chaotic dynamical system may be represented by a strange attractor, which appears to have a random structure but is actually an ordered dynamical mathematical object generated by an iterative process. A correlation dimension can be calculated which is a measure of the dimensionality of an attractor. A steady state system is represented by a point attractor which has very little variability, appears as a point on a phase space plot and has a dimension D equal to 0. A limit cycle is another attractor, and as the name suggests, represents a well-defined cyclical system, has a variation which can be plotted as a line, and a dimension D equal to 1. In general, if D is a non-integer, known as a fractal dimension, the underlying dynamics of the system may be represented by a strange attractor, also known as a chaotic attractor. A healthy chaotic heart should produce a strange attractor, whilst a limit cycle or a point attractor would correspond to a sick heart.

The main feature of chaotic attractors is their sensitivity to initial conditions. After a period of time it is increasingly difficult to predict the future evolution of the system from a given initial state. This is clearly the case with the heart. It varies in a seemingly random manner, and is sensitive to minor physiological changes which makes its future evolution impossible to predict with any degree of accuracy. Therefore I feel the R-R intervals of the data file can be considered to be a time series which lends itself to fractal analysis, using the correlation dimension, which itself can be considered a measure of the complexity of the underlying dynamical process. The Poincaré plot 36 represents a Poincaré section of a chaotic attractor, and the attractor's correlation dimension can be determined from the recorded R-R intervals.

According to one embodiment, the processing system 28 further includes correlation dimension software 40, such as INSITE which is produced by Insite Software of Berkeley Calif., and is used primarily by physicists for fractal analysis. The correlation dimension for a patient 22 is determined, as described hereinafter in the First Example, by the software 40 from the patient data file obtained by the R-R interval program 34 and provides a quantitative indication of the degree of heart failure. On the basis of present studies, a healthy patient produces a correlation dimension of approximately 8. The degree of heart failure in a patient is directly proportional to the extent to which a patient's correlation dimension varies from the correlation dimension of a healthy patient. In other words, the greater the patient's correlation dimension is below a predetermined level, the higher the level of heart failure. The correlation dimension derived from the R-R intervals provides a direct measure of the level of a autonomic activity in a patient 22. The apparatus 20 can be used to instantaneously assess a patient 22 and monitor the patients development over time.

Figure 12:
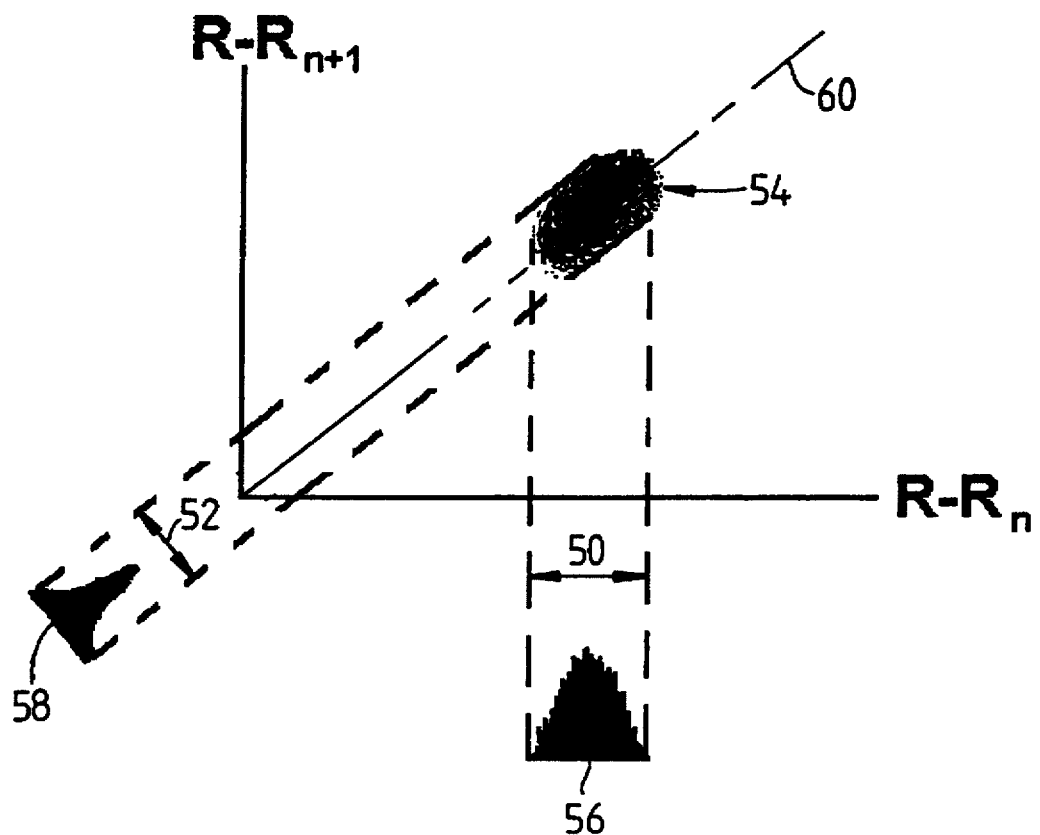
FIG. 12 is a Poincaré plot illustrating a relationship of the plot to histograms of R-R and ΔR-R intervals.
Figure 13:
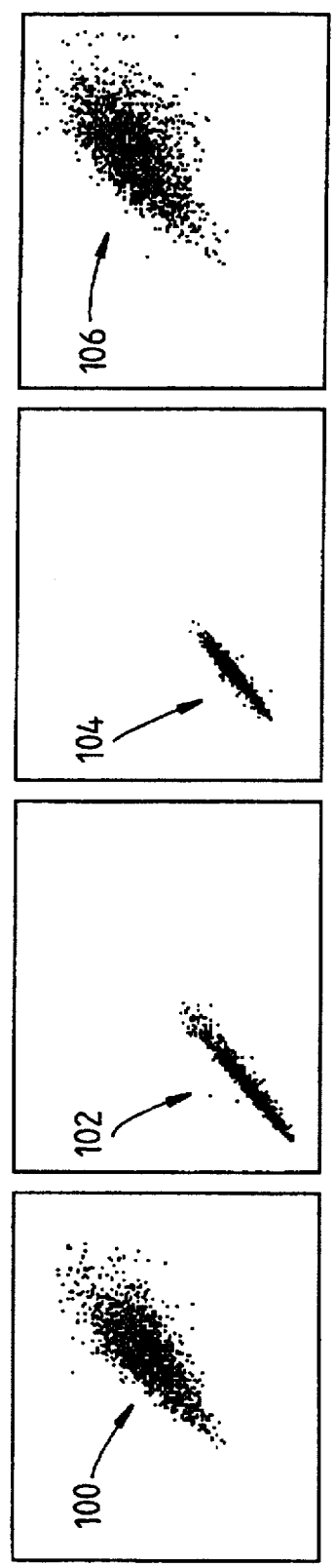
FIGS. 13 to 17 are Poincaré plots for a female subject having undergone four autonomic perturbation protocols.
Figure 14:
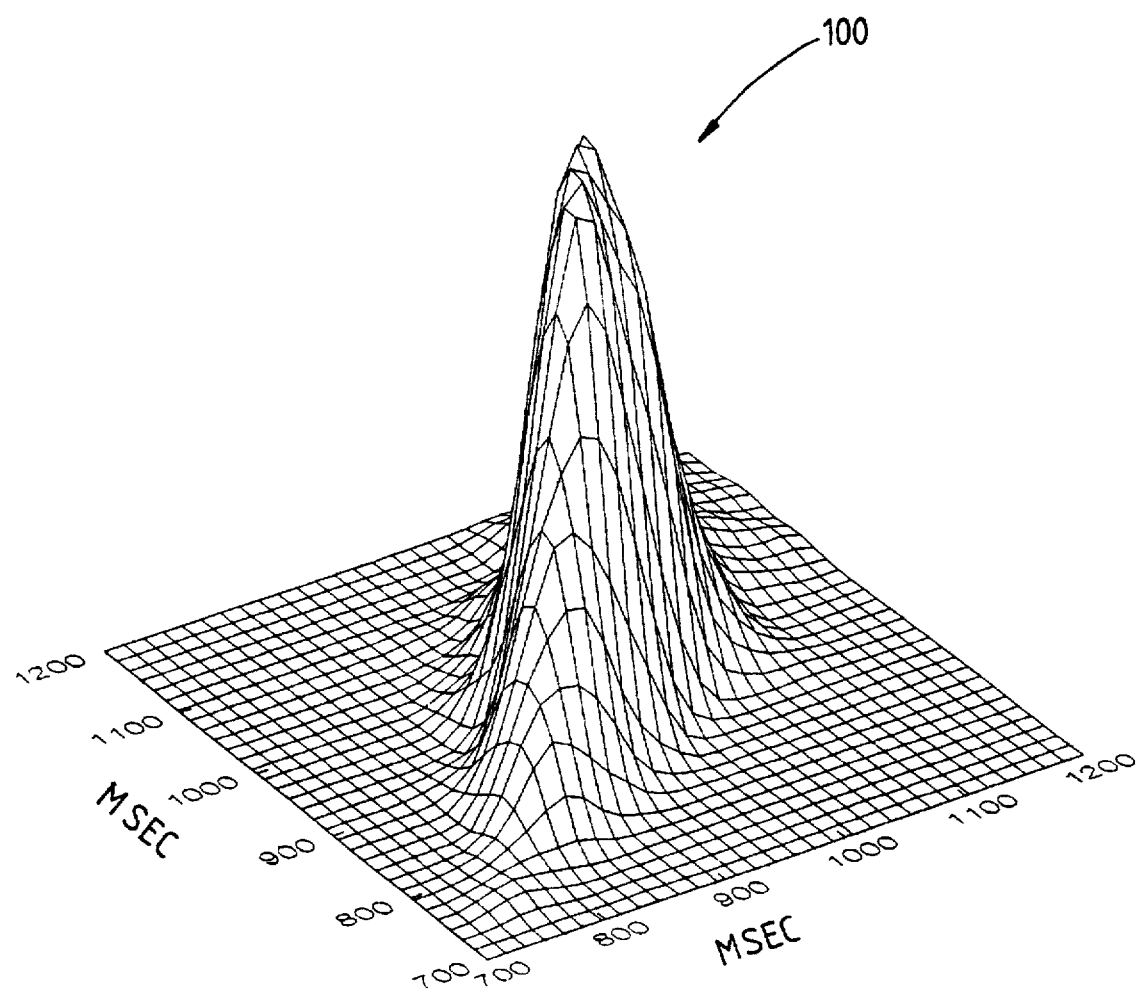
Figure 15:
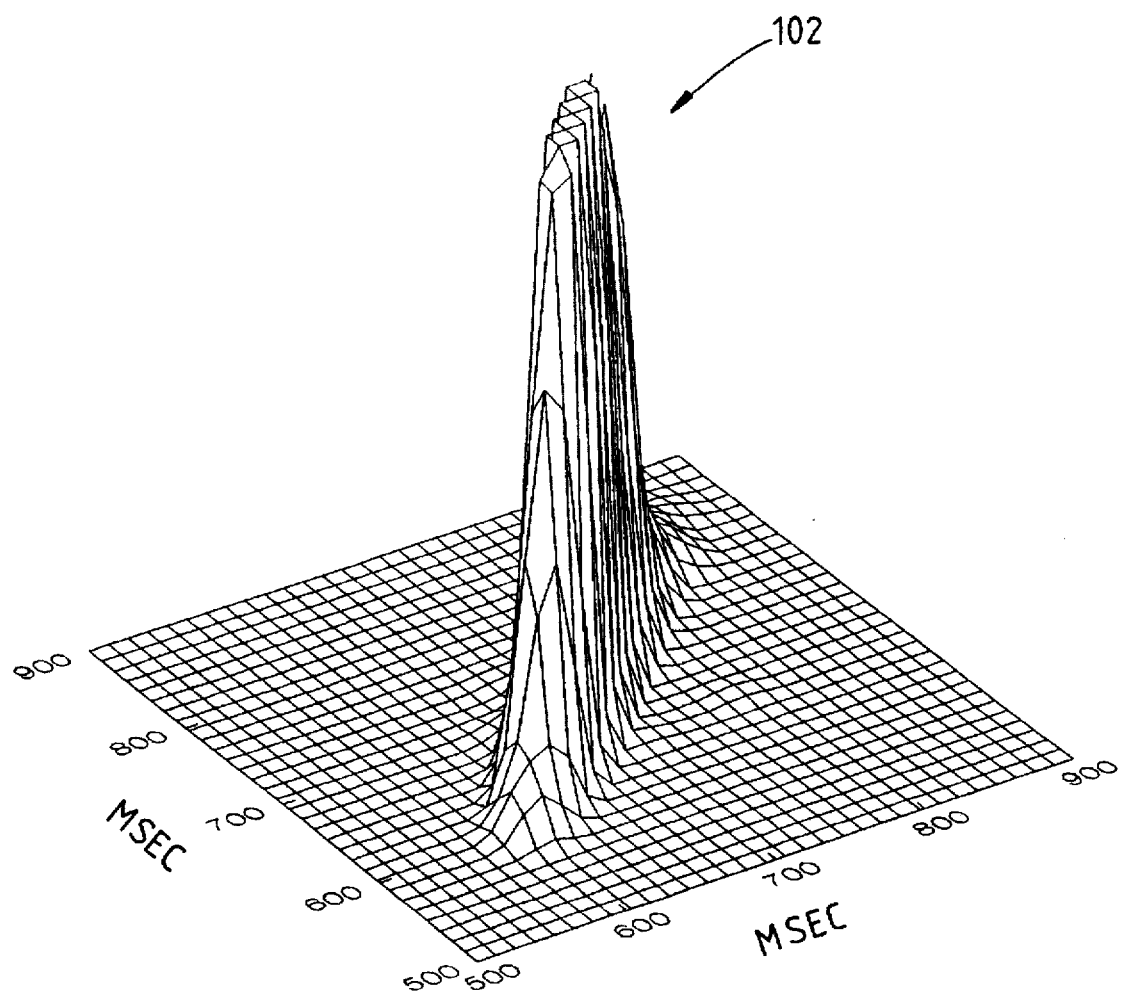
Figure 16:
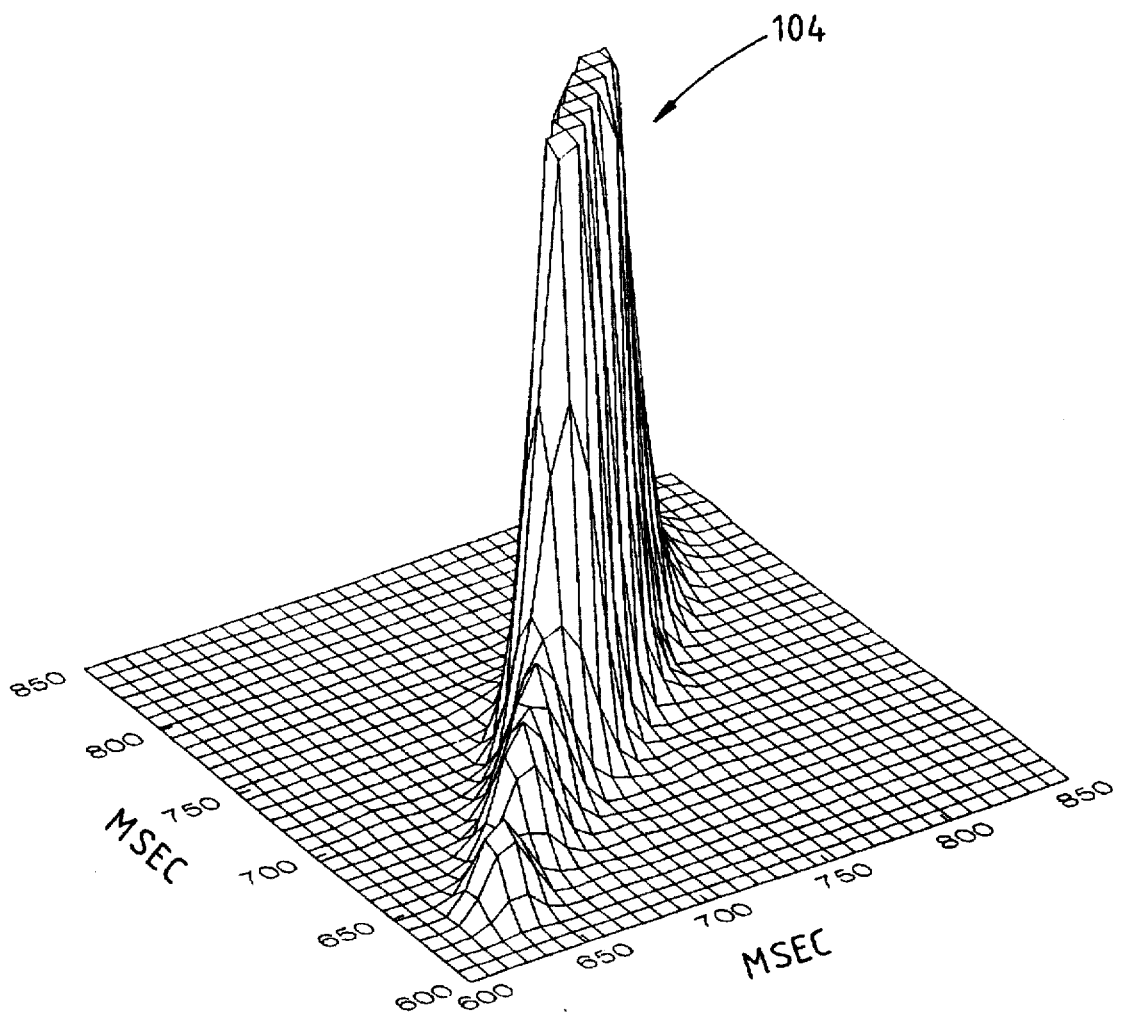
Figure 17:
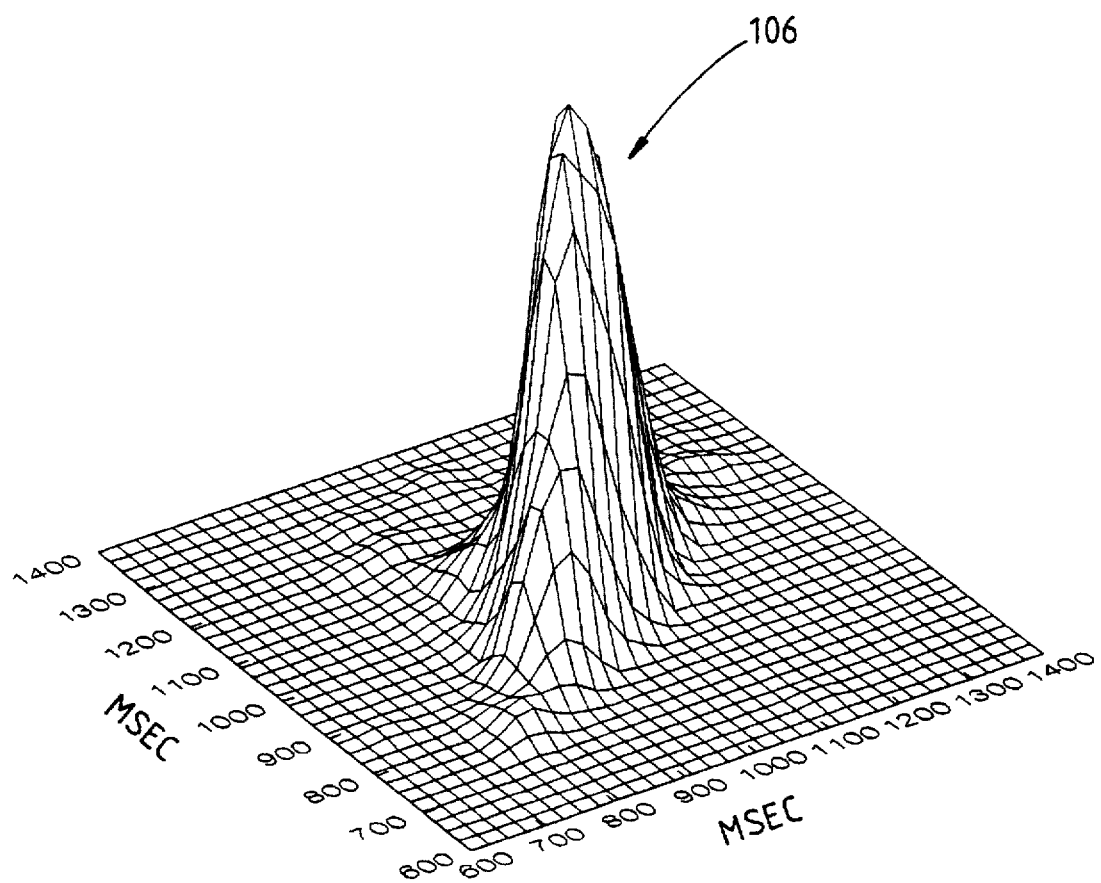

In addition to being able to quantify the level of sympathetic activity with the correlation dimension, I consider that the Poincaré plot provides a visual representation which enables the level of parasympathetic activity to be quantified. The width 52 of the Poincaré plot 54, as shown in FIG. 12, which is the spread along a line perpendicular to the diagonal line of identity 60 of the plot 54, represents the width or baseline spread of a histogram 58 of the ΔR-R intervals of the plot 54, as discussed in the Second Example hereinafter. The ΔR-R intervals are the differences between successive R-R intervals. This width or spread 52 relates to the standard deviation of the ΔR-R intervals which is equivalent to the standard deviation of successive differences (SDSD) or the root mean squared of successive differences (r-MSSD) of the R-R intervals, both of which have been considered in the past to provide a quantitative measure of parasympathetic activity. A measure of the width 52 of the Poincaré plot 54 therefore provides measure of the level of pure parasympathetic activity.

According to another embodiment, the processing system 28 further includes statistical software, such as SIGMASTAT by Jandel Scientific, U.S., which provides or is part of the software 40. The statistical software is able to produce histograms of the R-R intervals and ΔR-R intervals, and then produce standard deviations for the R-R intervals and the ΔR-R intervals. The last standard deviation provides a measure of pure sympathetic activity. The processing system 28 also produces a visual display of the Poincaré plot for a patient after a 20 to 40 minute monitoring interval. By using the width of the plot displayed, a determination can be made as to whether the patient has a low level of parasympathetic activity and therefore exhibits a degree of heart failure. Information obtained from the displayed plot 54 can be correlated with the statistical measures provided by the statistical software, in particular the standard deviation of the ΔR-R intervals to precisely determine the degree of heart failure. An Amlab™ workstation produced by Associative Measurements Pty. Ltd., Sydney, Australia may be used to run the software and produce the display.

FIRST EXAMPLE

Patients were selected at "random" from a large (10,000) semi-rural population when attending a general medical practice for routine medical attention and were accepted for testing after having given informed consent. The tests were done at various times of the day and subjects ranged in age from 14 to 88 years. Mean age was 63.7 years, standard error (SE) 1.28, and standard deviation (SD) 15.4 years. The patients were classified into two groups.

Group 1 patients (N=39) consisted of 13 female and 26 male subjects, aged between 14 and 84 years (mean age 51.8 years, SE 2.88) who were selected from the general population of patients. The selection criteria for this group was that they were clinically healthy, normotensive, had a normal ECG and were on no medications known to affect heart rate variability.

Group 2 patients (N=106) aged between 24 and 88 (mean age 68.1 years, SE 1.1) were selected from the same patient population. Included in this group were 47 male and 59 female patients who were selected on the basis of satisfying at least one of two criteria which were:
1. Abnormal ECG as per the report from Burdick Elite interpretive ECG machine 24 and confirmed by a cardiologist.
2. Patients already on medication for hypertension, heart failure, diabetes or ischaemic heart disease. Patients taking digitalis, ACE inhibitors, β-adrenergic blocking drugs, calcium channel blocking agents and psychotropics were included in the study. Eight patients in atrial fibrillation (AF) were excluded. One patient with marked sinus arrhythmia had a random pattern similar to AF but was included for completeness.

Group 2, as shown in Table 1, comprised three further subgroups. Group 2a included 24 heart failure patients in different degrees of failure and classified according to the New York Heart Association (N.Y.H.A.) guidelines, Class IV representing the group with the highest degree of heart failure (mean age 75 years, SE 1.4). Sixteen patients were taking digoxin and frusemide. Four patients were taking low dose ACE inhibitors and frusemide. Four patients were on frusemide alone. Group 2b consisted of 56 patients with hypertension on a variety of medications (mean age 67.4, SE 1.3). Group 2c included 26 patients with various medical conditions (mean age 64.1, SE 2.8).

TABLE 1

| GROUP 2 PATIENTS | | |
|---|---|---|
| Group 2a. Heart Failure Group | N.Y.H.A. Classification | Number of Cases |
| N = 24 mean age 75.0 years | I | 6 |
| SD = 6.92 | II | 10 |
| SE = 1.41 | III | 3 |
| | IV | 5 |
| | TOTAL | 24 |
| Group 2b. Hypertensives | Classification | Number |
| N = 56 mean age 67.4 | No subgroups | |
| SD = 9.8 SE = 1.3 | TOTAL | 56 |

TABLE 1-continued

| GROUP 2 PATIENTS | | |
|---|---|---|
| Group 2c. Others | Diagnosis | Number |
| N = 26 mean age 64.1 | ECG abnorm. | 4 |
| SD = 14.5 SE = 2.84 | angina | 4 |
| | previous AMI | 1 |
| | arrhythmia | 5 |
| | type 2 diabetes | 2 |
| | COAD/asthma | 2 |
| | stress related | 4 |
| | others | 4 |
| | TOTAL | 26 |

In order to ensure the calculated correlation dimensions accurately reflect internal activity of the neurohumoral mechanism controlling the sinus node, external influences on activity of the autonomic nervous system needed to be minimised. Fixed time samples of an isolated dynamic system are normally required for dynamical analysis of an experimental time series, and although this mathematical requirement is difficult to achieve in biological studies, the patients were required to rest quietly on a couch 32 for ten minutes prior to collection of R-R interval data. R-R interval versus time tachograms were used to check that a patient 22 was at rest and stationary before data was accepted. 1500 to 2000 R-R interval data points were required to calculate a correlation dimension for a patient 22, and data samples were taken for 24 to 40 minutes. The tests were scrutinised during the recording process to prevent artefact or a malfunction corrupting data. Some artefact was inevitable, but a standard filtering algorithm could be used to remove outlier influence on the standard deviation calculation and Fourier analysis. Each data set was examined from the perspective of the Poincaré plot, tachogram and histogram before the standard deviation was accepted as an appropriate measure of the spread of data in the filtered set. As well as the visual inspection of the tachogram and histogram, a Fourier analysis was performed on the time series to check for introduced artefact signals. Poincaré plots and correlation dimensions were generated using the raw, unfiltered data.

Calculation of a correlation dimension, as described in "Measuring the Strangeness of Strange Attractors", by Grassberger P. and Procaccia L, Physica 1983; 9D pages 189–208, is conventionally performed on data which has been collected at fixed sample periods. For the R-R interval samples, if the heart rate is sampled every beat, the time lag (τ), being the interbeat interval, is not fixed in time as required in conventional techniques, but I feel it can be considered to be fixed in topological space at the plane of the Poincaré section. Therefore I consider that an attractor can be reconstructed from the Poincaré section using τ as the lag.

A curve log C(r) (correlation integral) vs. log r (radius of hypersphere) was evaluated and plotted using the software 40 on the basis of the following algorithm:

$$C(r) = \lim_{N \to \infty} \sum_{i,j=1}^{N} \theta(r - |\zeta_i - \zeta_j|),$$

where
$\zeta_i = (x(t_i), x(t_i + \tau), \ldots x(t_i + (m-1)\tau)$
N is the number of samples
m is the embedding dimension, and
θ is the Heaviside function (normally 1, but 0 if $r - |\zeta_i - \zeta_j|$ is negative)

The radius of the hypersphere is determined by the software 40 on the basis of the estimated size of the attractor reconstructed from the time series $\zeta_i$ for i=1 to N. The time delayed vectors $\zeta_i$ are constructed from the ECG samples with increasing values of the embedding dimension m.

A linear segment of the curve was determined by visual inspection, and the slope of this segment, which is a correlation dimension, was determined by the least squares method. The calculation of a correlation dimension was iteratively repeated for increasing values of m, to a maximum of 24, until an asymptote value of the correlation dimensions could be determined. Higher embedding dimensions were used for some patient data to confirm the asymptote value of the correlation dimension. After obtaining sufficient correlation dimensions for a data set, a second order polynomial curve fitting algorithm of a standard curve fitting program was used to fit a curve to the dimensions to assess the asymptotically stable correlation dimension. The correlation dimension vs. m curve normally asymptoted to a horizontal line. The asymptote value was accepted as the patients correlation dimension if the sample correlation coefficient was greater than 0.95. If the r value was less than 0.95 the correlation dimension was not accepted.

The total population of patients showed a wide spread of patterns ranging from very tight clusters to bizarre and complex shapes. Patients were kept at rest on a couch whilst being monitored, with the result that the healthy group displayed Poincaré plot patterns which lacked the characteristic "stem" seen in the patterns of healthy subjects in the American Holter monitoring study, described previously. 139 Poincaré plots (96%) were able to be quantified using the correlation dimensions whereas the standard deviation of the heart rate variability data could be applied to only 97 (67%) studies. Inspection of the Poincaré plot almost always showed a main cluster with a variable number of outliers which were due to ectopic or arrhythmic activity. These outliers were removed to prevent excess variance in the standard deviation measure.

A subjective decision was made on the degree of filtering required to remove artefact and yet not destroy the validity of the standard deviation. Patients in Group 2 (study group) showed more ectopic activity than those in Group 1, but no significant correlation was found between the number of ectopics, patient subgroup or degree of heart failure. Of importance was the observation that the presence of outliers did not influence the correlation dimension measure. It proved to be extremely robust in contrast to the Fourier analysis and standard deviation measure which were extremely sensitive to even the occasional ectopic or artefact.

All healthy subjects (N=39) of Group 1 shared a characteristic pattern in their Poincaré plot which displayed a clustering of points around a central core, reminiscent of a galaxy of stars in space. With reference to Table 2, there was no comet shapes in this group. As expected, the degree of heart rate variability as measured by the standard deviation in the time domain showed a reduction with increasing age. There was no correlation between the correlation dimension and age. The cluster pattern was subdivided into three groups according to the standard deviation of the data spread. Heart rate variability was easily quantified with the standard deviation due to the normal distribution of R-R intervals in the healthy group.

With regard to Group 2, it soon became clear that a major characteristic of the second group was the lack of normal cluster Poincaré plots. The standard deviation was not a reliable measure of the heart rate variability in this group.

The Poincaré plot pattern replaced the unreliability of the standard deviation. It provided a clear, unambiguous image of the data as it was being generated and because it compressed the data into one morphologically distinct grouping it encouraged an easy classification based on pattern characteristics.

Analysis of these patterns showed a preponderance of "complex" patterns in the heart failure group and the arrhythmia/ischaemia subgroup. 31 patients (29%) displayed complex patterns which consisted of several clusters of points, often with central areas reminiscent of tight clusters or cigar shapes. The histograms of these patterns showed a main group with one or two minor clusters. These patterns occurred characteristically in patients who generated multiple ectopics. A characteristic feature of these Poincaré plots was the appearance of echo groups whenever ectopic activity delayed the next QRS complex. This group had a mean reduction in correlation dimensions consistent with an overall increase in sympathetic activity.

Within Group 2a (heart failure), the "type" of pattern correlate to the degree of cardiac dysfunction as measured by the N.Y.H.A. classification. The correlation dimension was an objective measure and overcame the difficulty of a subjective assessment of pattern complexity. Within this group the correlation dimension was negatively correlated to the N.Y.H.A. classification. The standard deviation was not a predictor of cardiac status.

In Group 2b (hypertensives) the correlation dimension showed no predictable pattern in this heterogeneous group.

Data from Group 2c patients were a mixed population with a variety of pattern types. Of interest was the arrhythmia subgroup which always generated a complex pattern. This was associated with a low correlation dimension suggesting sympathetic overactivity.

The Poincaré plots taken from both groups combined (N=145) can be classified as follows.

Figure 3A:
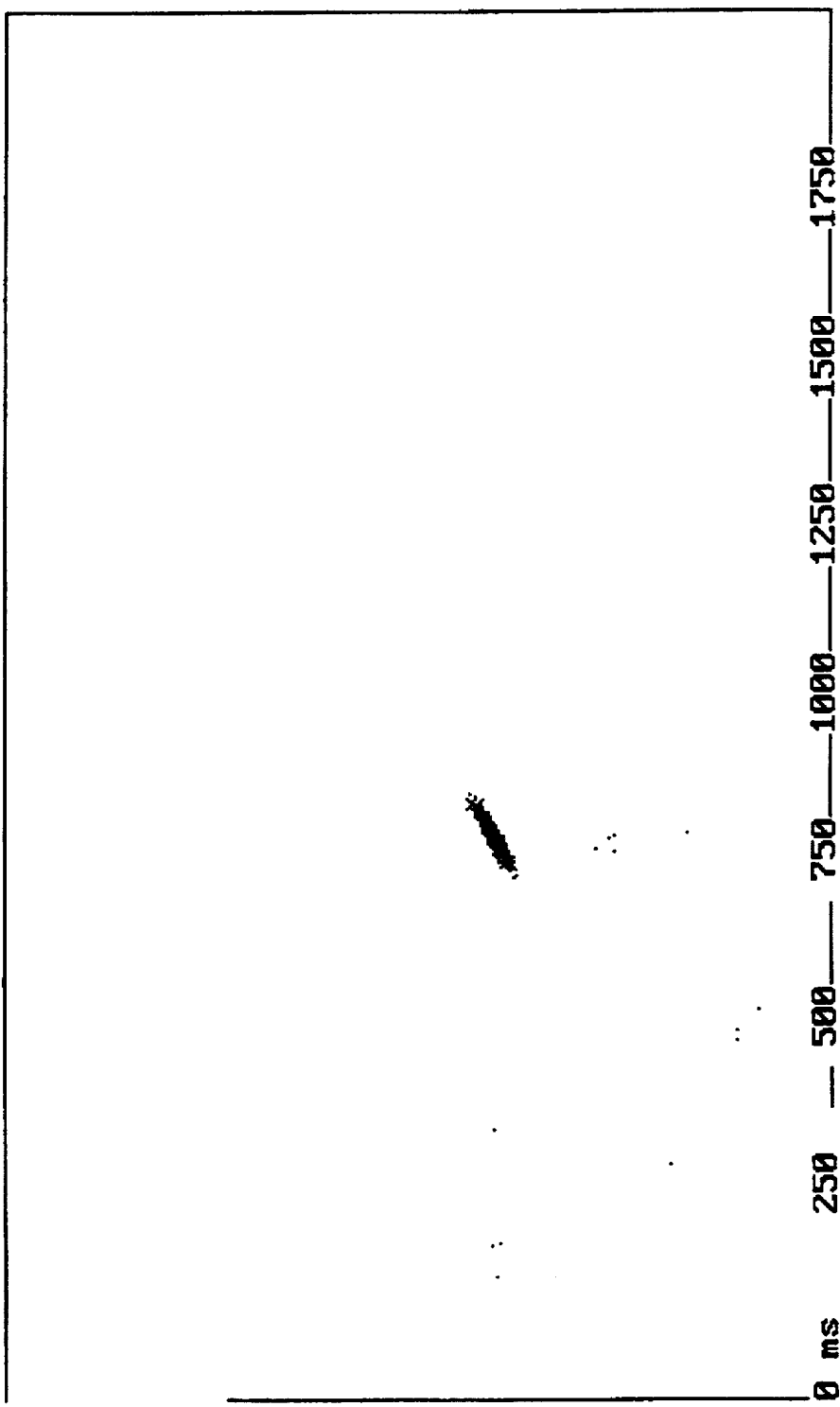
FIGS. 3A and 3B are tight cluster Poincaré plots produced by the apparatus.
Figure 3B:
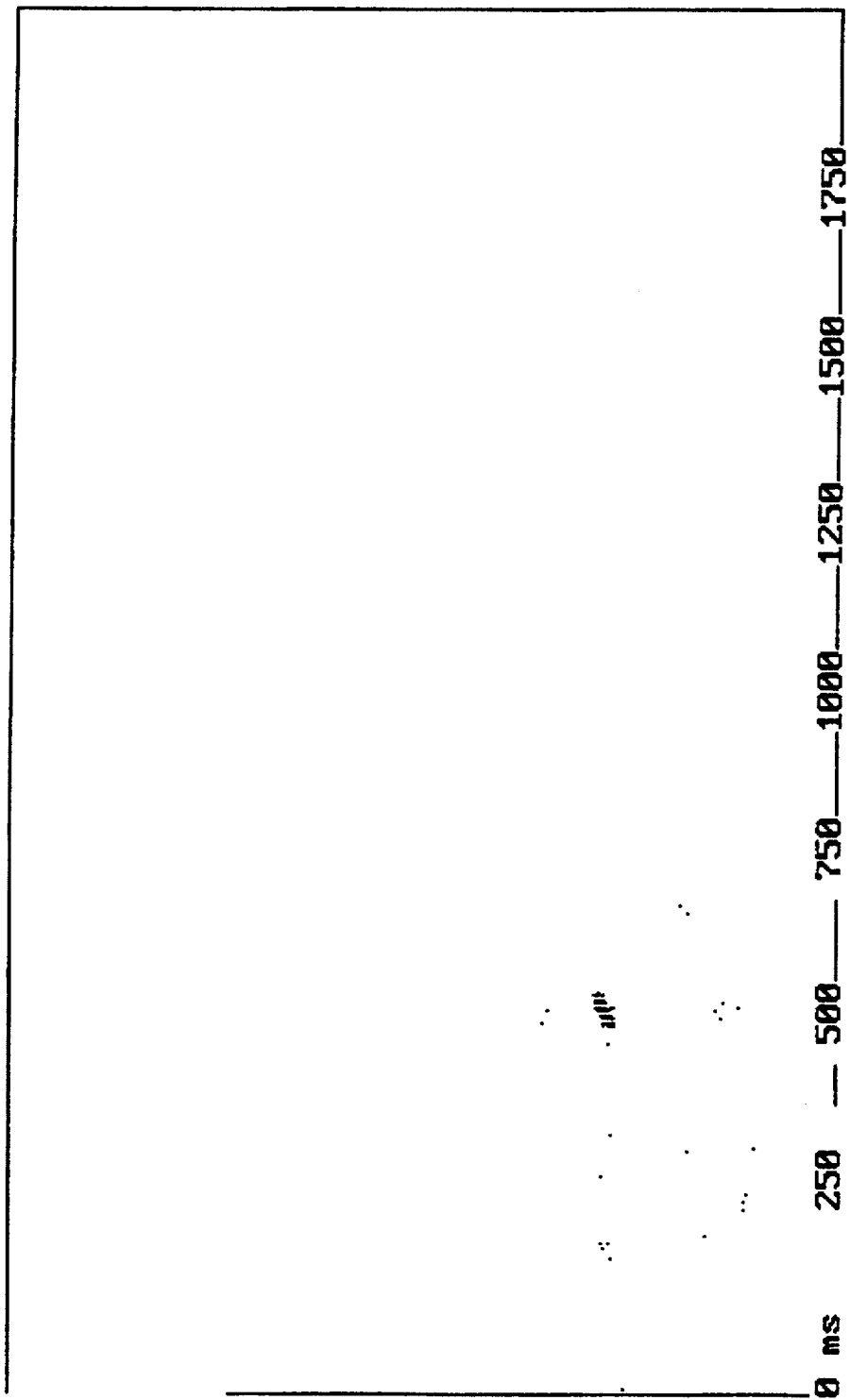

A tight cluster, as shown in FIGS. 3A and 3B, (N=21) was defined as data with a standard deviation of 0 to 30 ms. Most of the data resembled a normal distribution histogram with very little variation in the interbeat interval (N=15, mean correlation dimension=7.9±1.5 SD). A significant proportion of these plots were truly random rather than chaotic (N=6, 28% of all TCL clusters). This may reflect the loss of response of the sinus node to autonomic control. Three subjects in the healthy group produced tight clusters with a mean correlation dimensions of 9±1.5 SD with one tight cluster not producing an acceptable correlation dimension value. Whereas tight clusters in Group 2 tended towards a low correlation dimensions suggesting a physiologically distinct group.

Figure 4A:
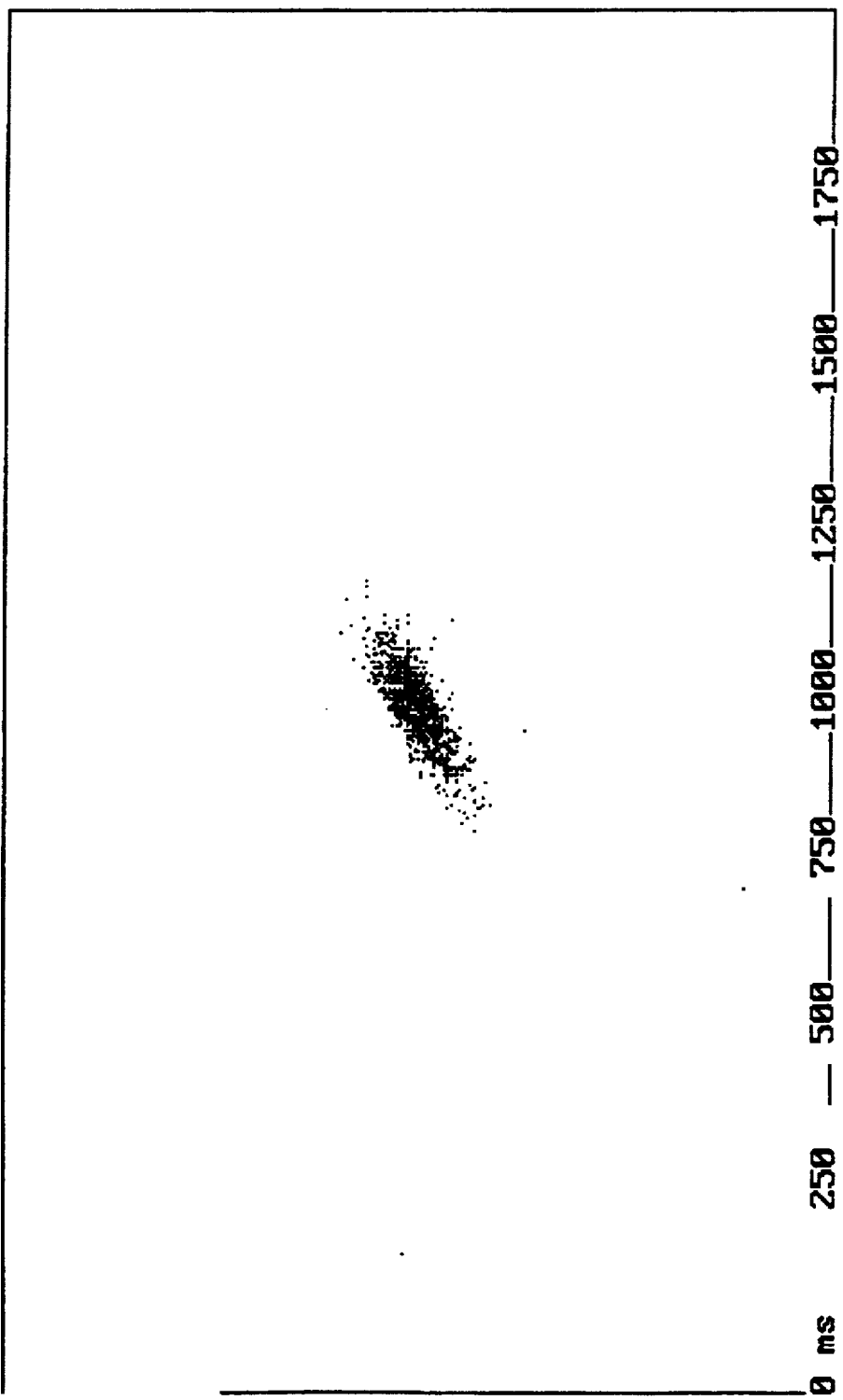
Figure 4B:
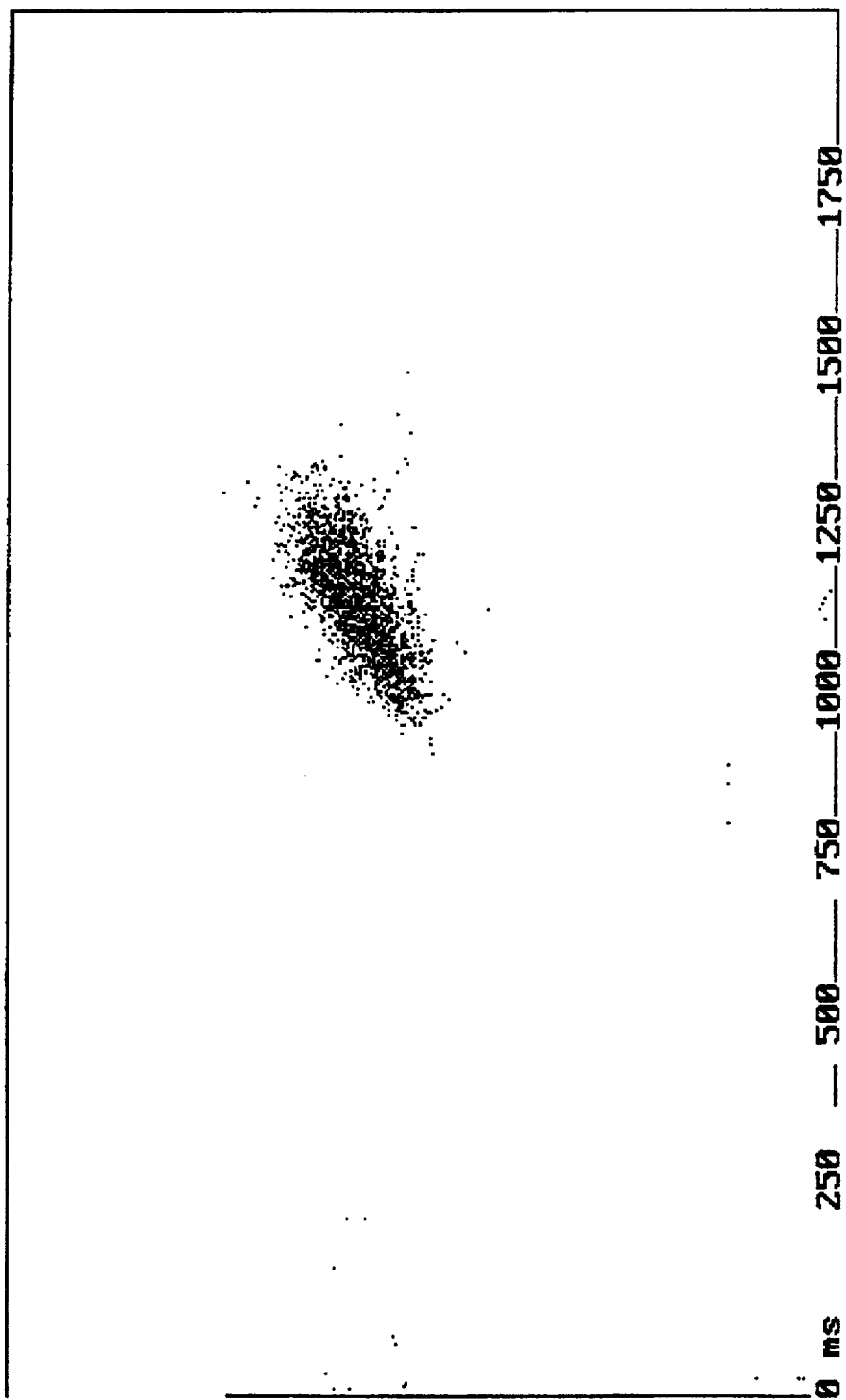

A cluster, as shown in FIGS. 4A and 4B, relates to a group showing a normal distribution with standard deviation of 31 to 80 ms (N=74, mean correlation dimensions=8.0±1.5 SD). This was the predominant pattern in the healthy control group.

Figure 5:
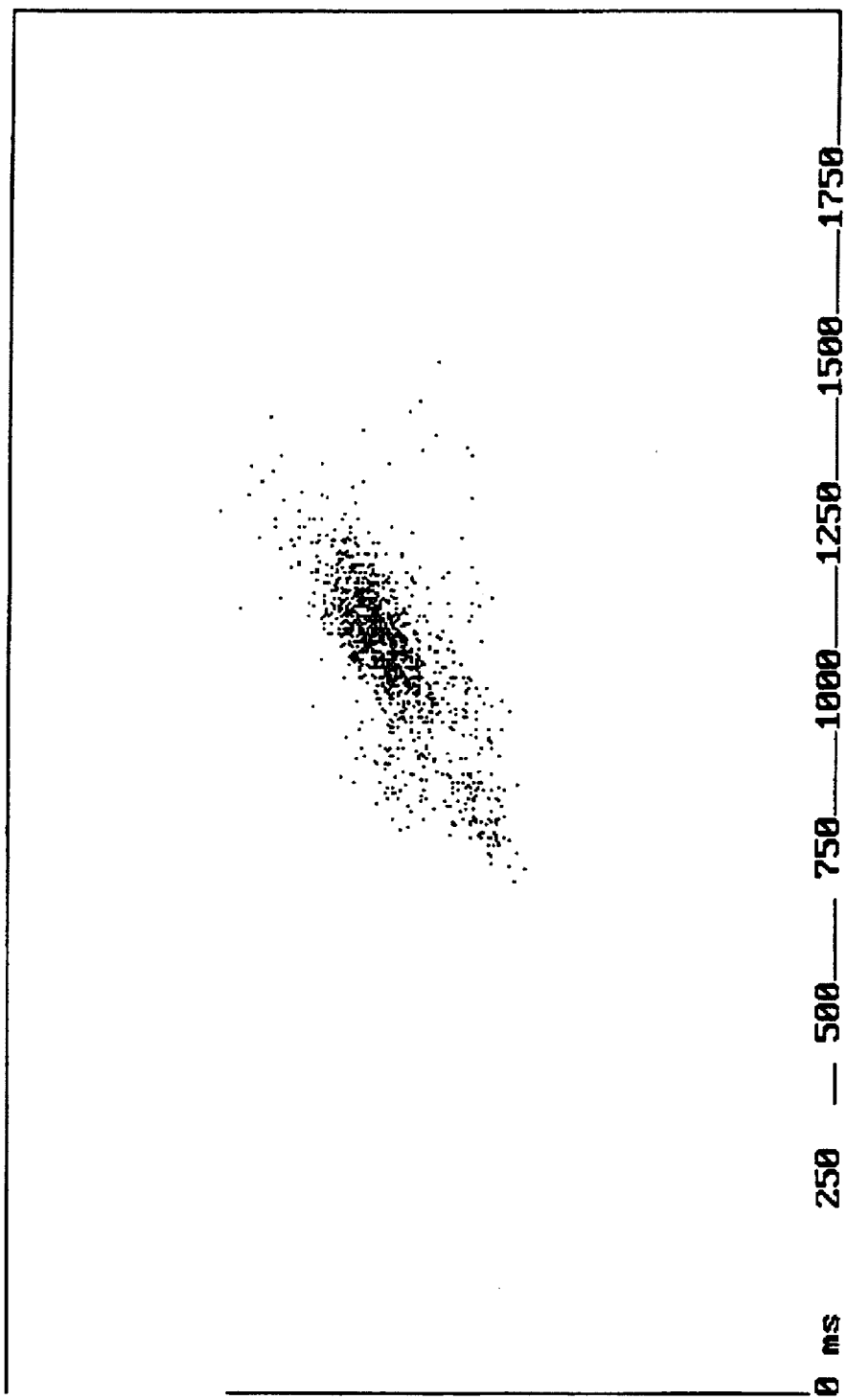
FIG. 5 is an open cluster Poincaré plot produced by the apparatus.

An open cluster pattern, as shown in FIG. 5, is characterised by a spread of data with a standard deviation greater than 80 ms (N=3, mean correlation dimension=8:87±1.0 SD). The high degree of variability of the heart rate in this group was reflected in an increase in the correlation dimension. This pattern appeared in two very fit subjects consistent with a reduction in sympathetic and increase in parasympathetic activity.

Figure 6B:
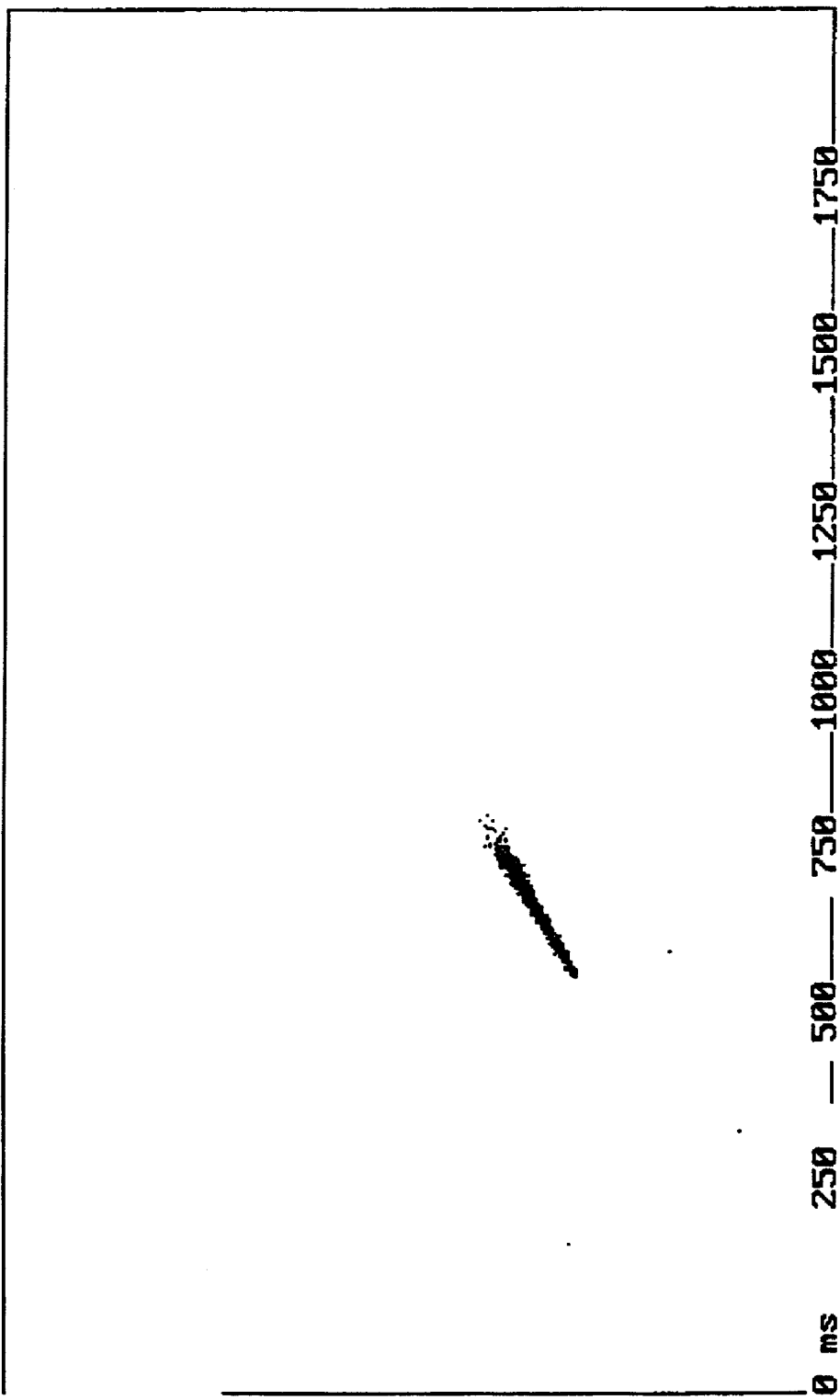

A cigar or torpedo pattern, as shown in FIGS. 6A and 6B, does not have a normal distribution of data making the standard deviation an in appropriate measure to use. This pattern is the result of minimal deviation of heart rate in the short term but a gradual change over a longer time suggesting significant low frequency sympathetic modulation. The correlation dimension of this group was also significantly reduced (N=8, mean correlation dimension=7.28±1.2 SD).

Figure 7:
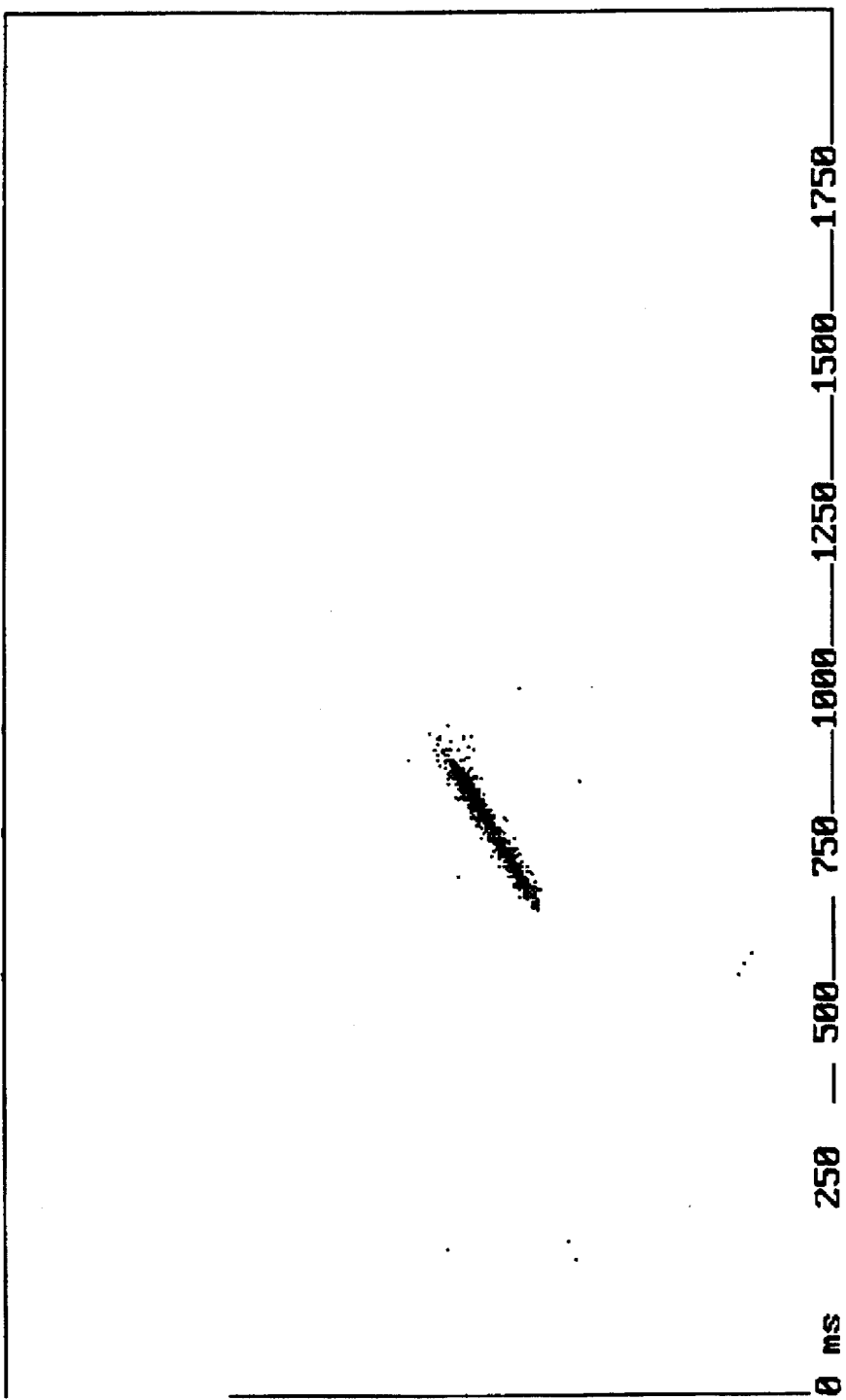
FIG. 7 is a fat cigar Poincaré plot produced by the apparatus.

A fat cigar, as shown in FIG. 7, indicates that for any R-R interval, the next R-R interval deviates more than in the cigar pattern suggesting a reduction in sympathetic dominance with more obvious high frequency parasympathetic modulation (N=3, mean correlation dimension=7.1±1.3 SD).

Figure 8C:
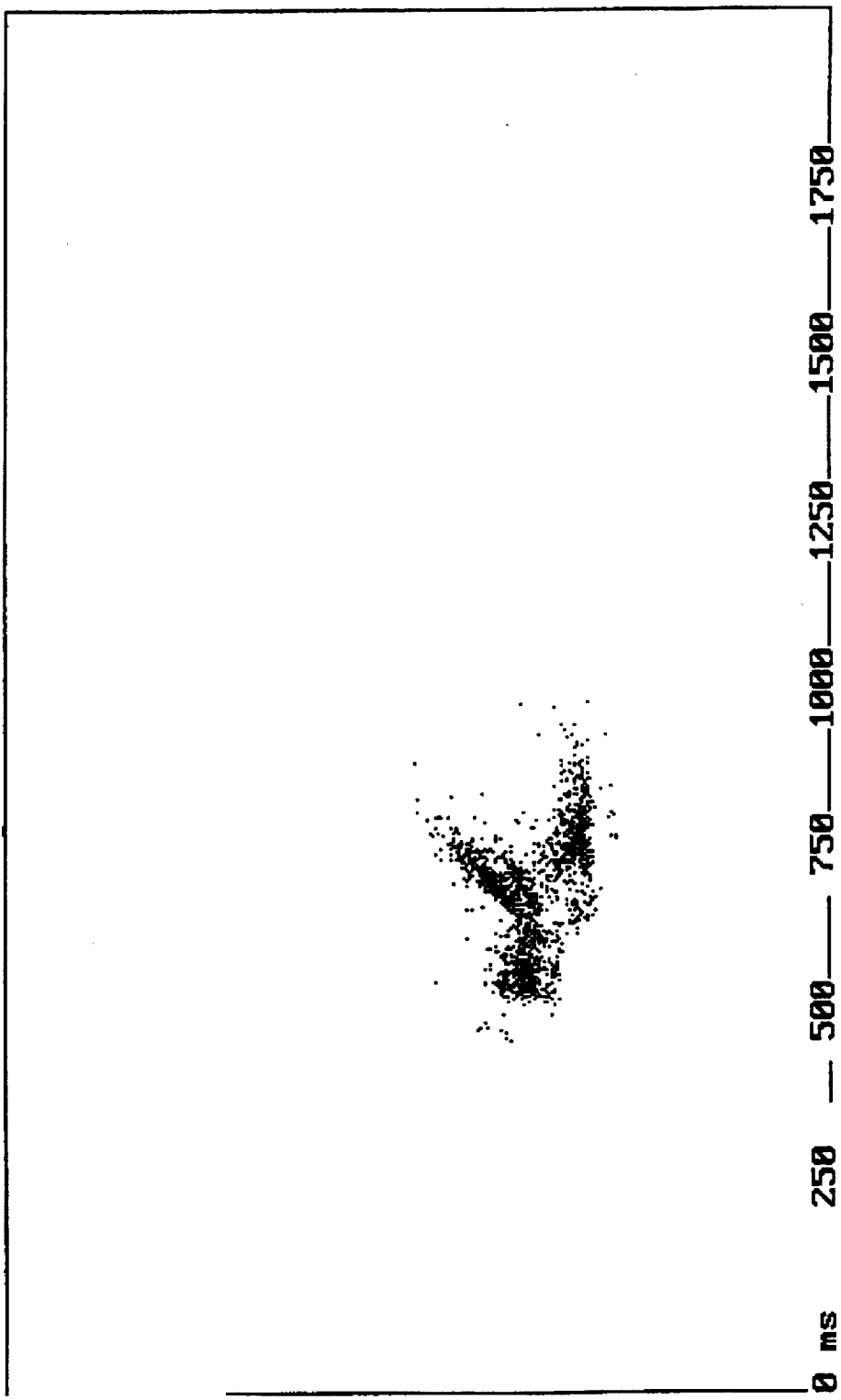

A complex pattern, as shown in FIGS. 8A, 8B and 8C, characteristically shows a central core reminiscent of the normal data spread with satellite clusters resulting from the ectopic activity and the corresponding "echo" of the plotting process. These patterns occurred commonly in two groups of patients, (1) severe heart failure, and (2) patients complaining of palpitations. The correlation dimension showed a significant reduction in both groups (N=31, mean correlation dimension=6.58±1.7 SD).

Figure 9B:
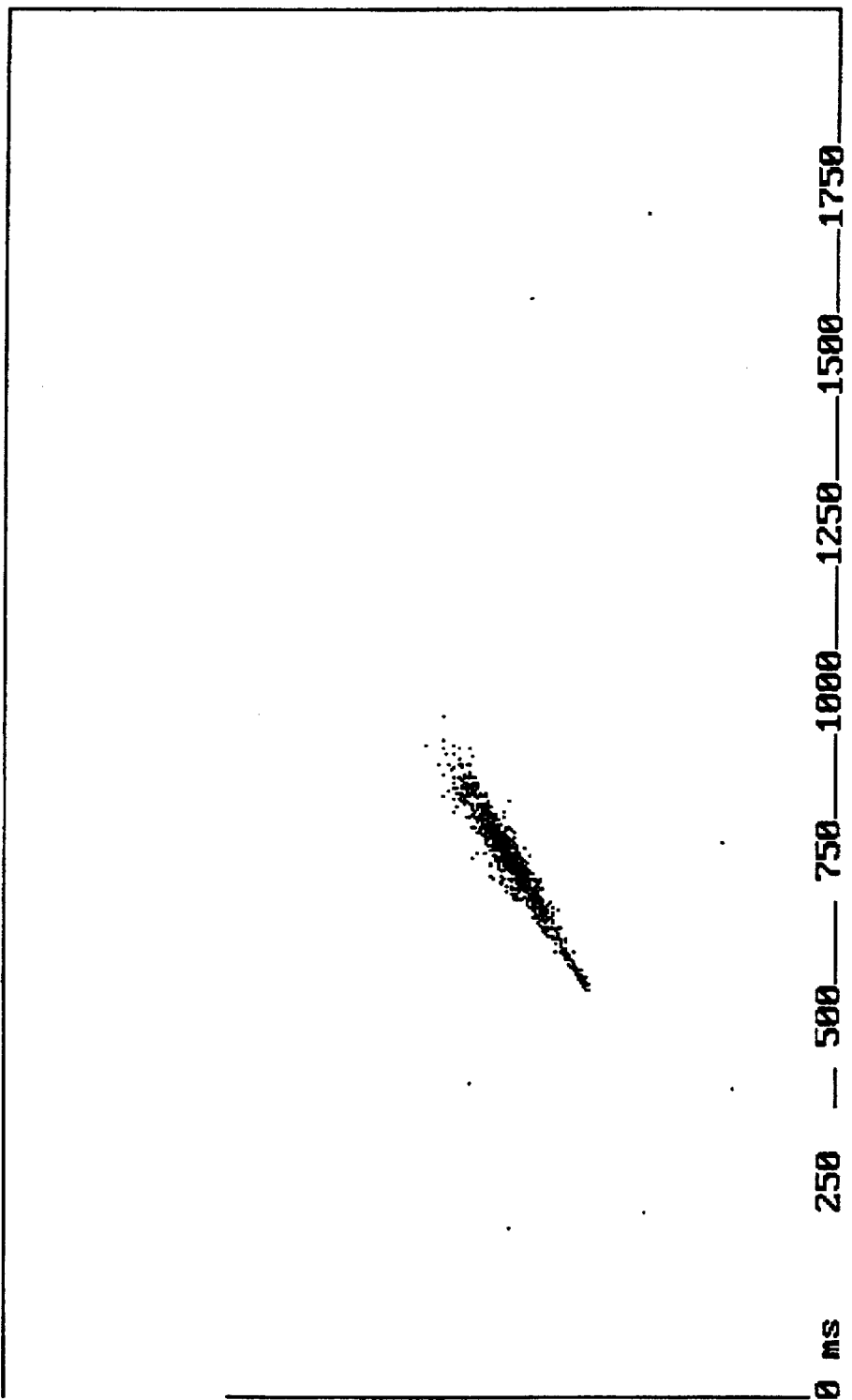
Figure 9C:
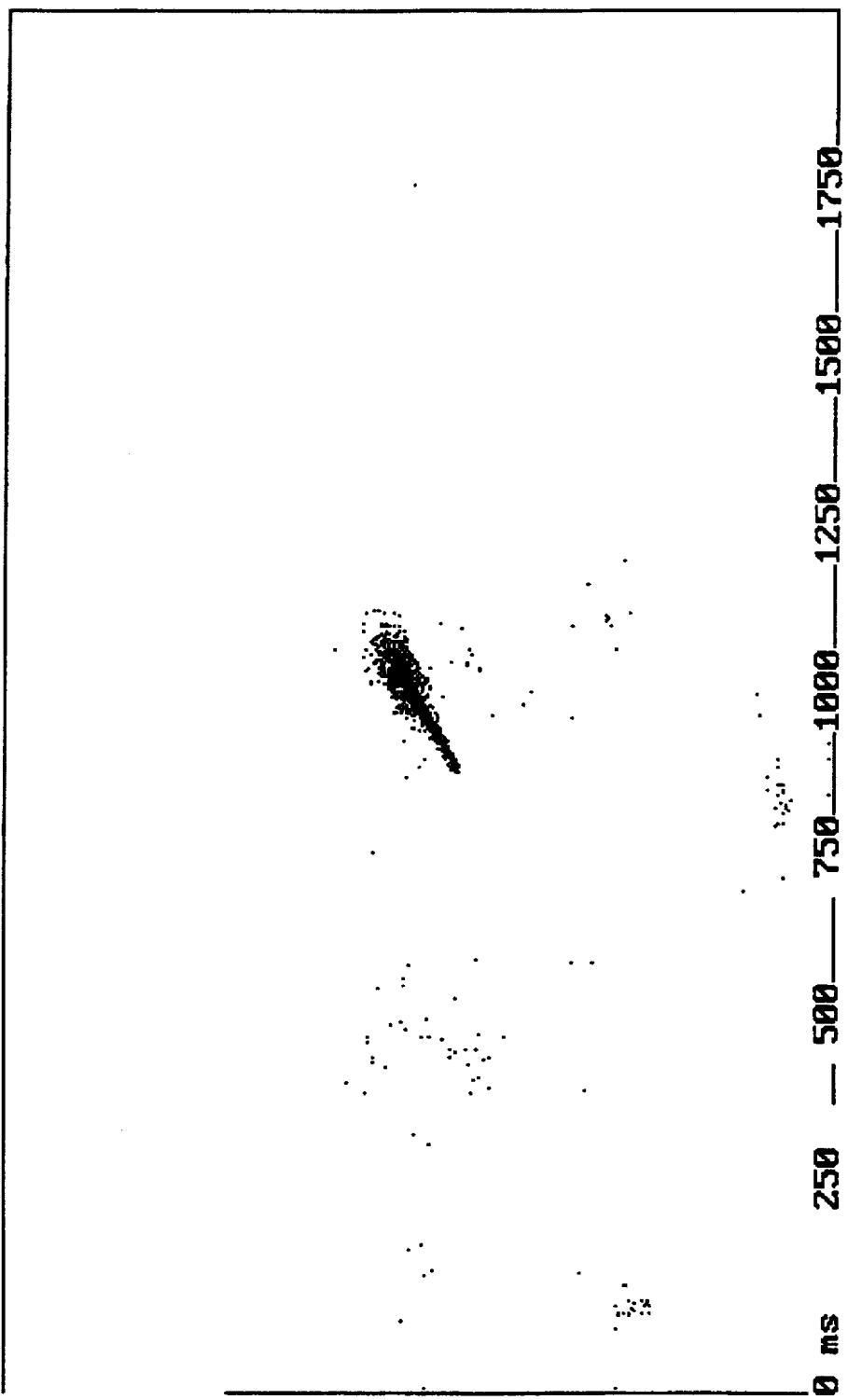

A comet shape, as shown in FIGS. 9A, 9B and 9C, was only seen in Group 2, evenly distributed through the subgroups. They all produced a low correlation dimension (N=3, mean correlation dimension=6.5±1.4 SD).

Figure 10:
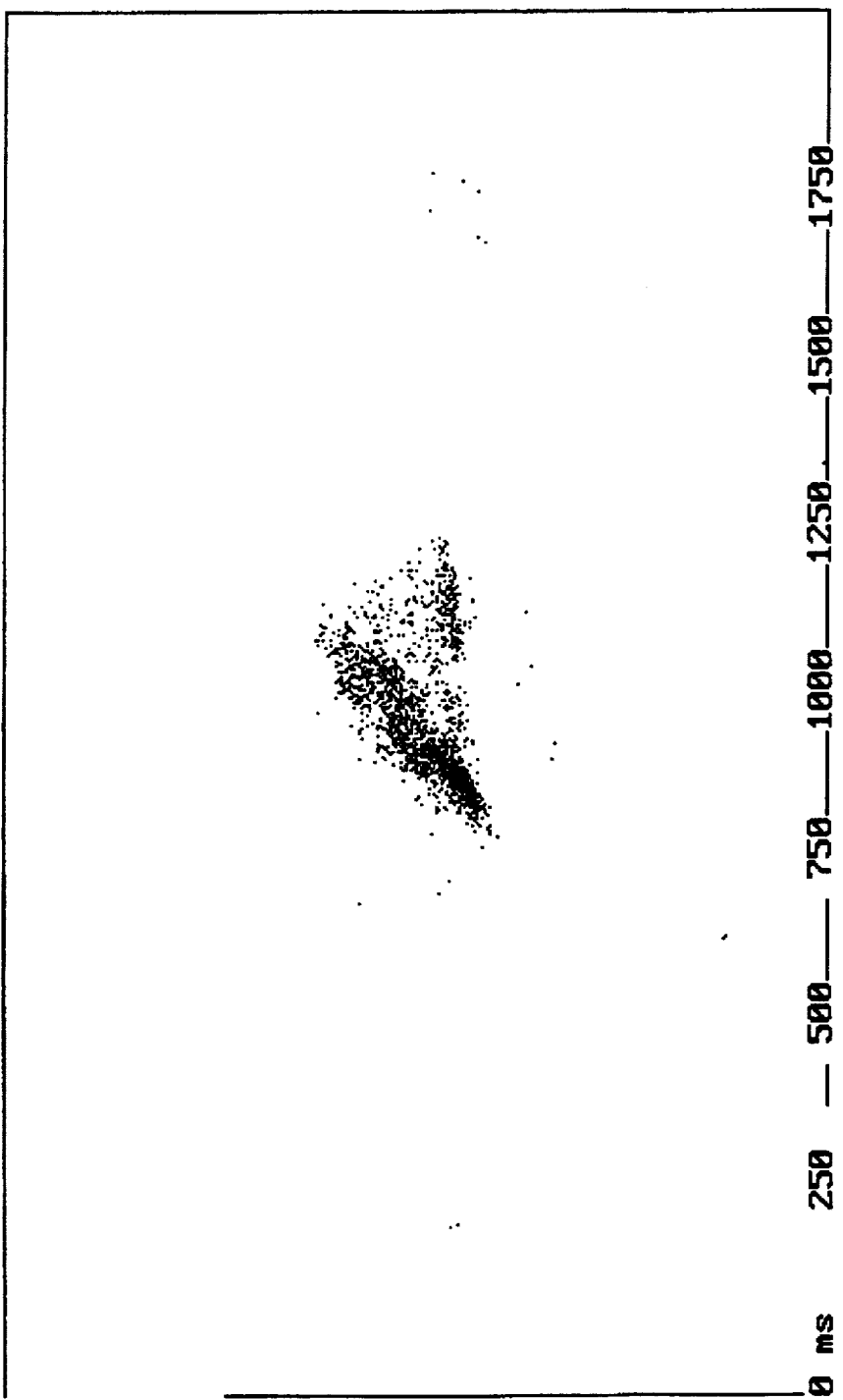
FIG. 10 is a fan shape Poincaré plot produced by the apparatus.

A fan shape pattern, as shown in FIG. 10, was uncommon (N=2, mean correlation dimension=5.55±0.9 SD) but they had the lowest correlation dimension. One fan was produced by a patient with severe Class IV heart failure whilst another fan shape, albeit with a larger spread, was produced by an anxious, treated, hypertensive patient.

Figure 11A:
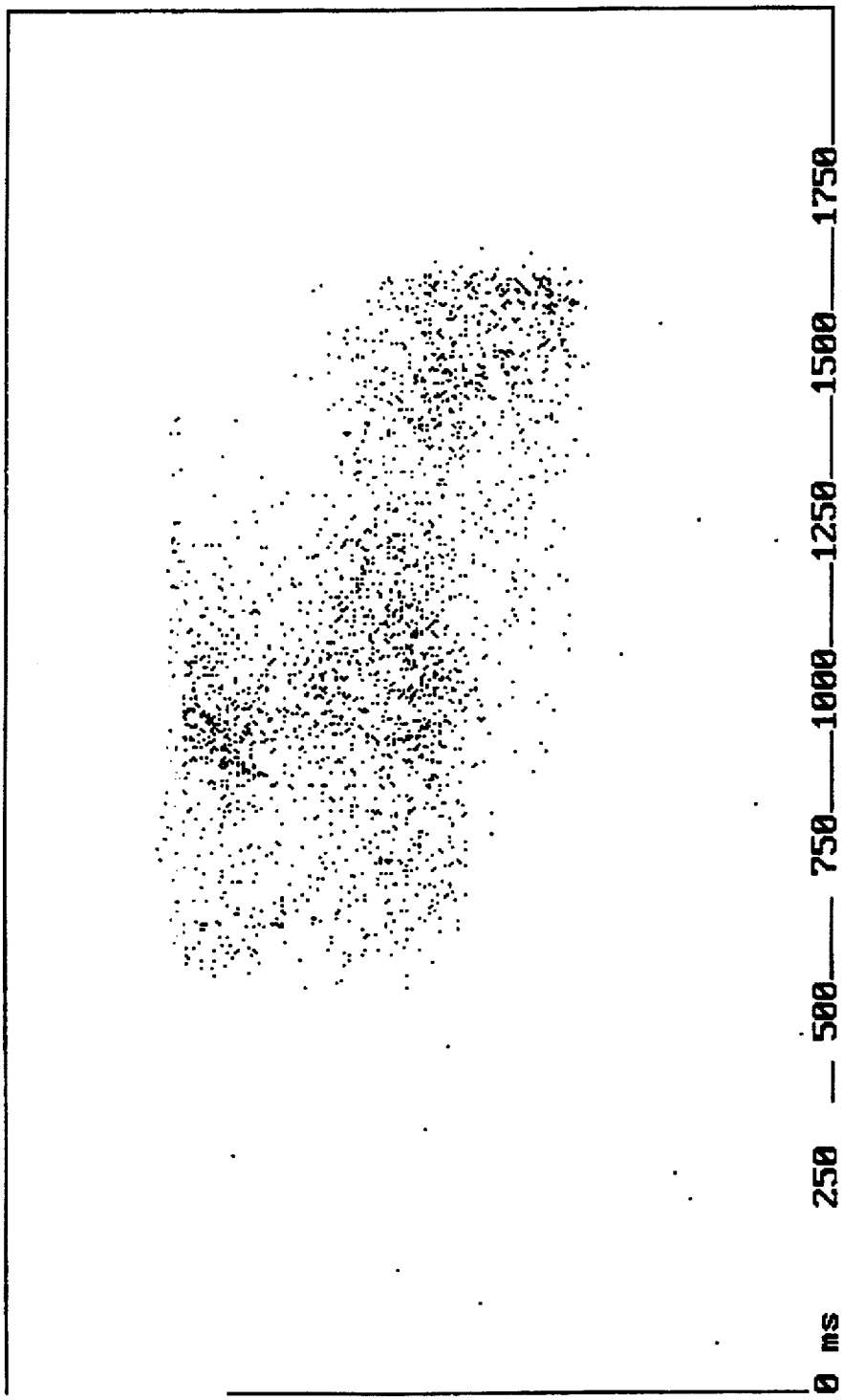
FIGS. 11A and 11B are random pattern Poincaré plots produced by the apparatus.
Figure 11B:
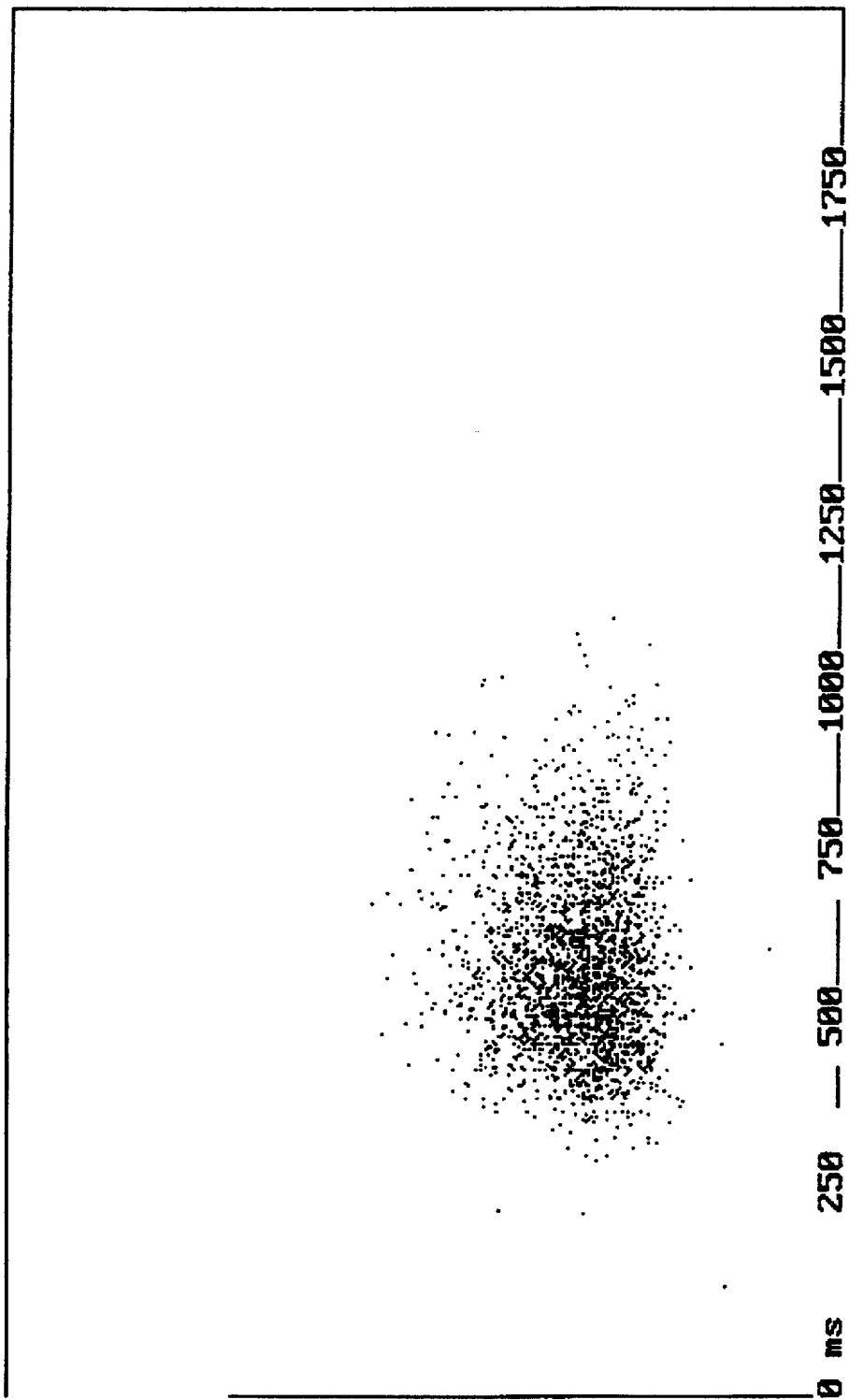

A random pattern, as shown in FIGS. 11A and 11B, appeared in patients with atrial fibrillation (N=8) and in a patient with a marked non-periodic arrhythmia. The correlation dimension did not converge to a clear asymptotic value in one patient at a maximum embedding dimension of 28. This suggests that the attractor is either of a very high dimension or it is in fact displays random behaviours. Two patients in atrial fibrillation displayed seemingly random Poincaré plots but produced correlation dimensions of 6 and 8.

TABLE 2

POINCARÉ PLOT PATTERNS IN NON-AGE MATCHED GROUP (N = 145)

| Variable | Group 1 | Group 2 | Correlation Dimension mean ± SD |
|---|---|---|---|
| No. of Patients | 39 | 106 | |
| Mean Age | 52.6 years ± SE 2.72 | 68.1 years ± SE 1.1 | |

| Poincaré plot patterns | Group 1 | | Group 2 | | |
|---|---|---|---|---|---|
| Open Cluster (81–120 ms) | 3 | 7.7% | 1 | 1% | 8.87 ± 0.98 |
| Cluster (31–80 ms) | 32 | 82% | 43 | 41% | 8.0 ± 1.46 |
| Tight Cluster (0–30 ms) | 4 | 10.3% | 14 | 13% | 7.86 ± 1.49 |
| Cigar Shape | 0 | 0% | 8 | 8% | 7.28 ± 1.22 |
| Fat Cigar Shape | 0 | 0% | 3 | 3% | 7.06 ± 1.35 |
| Complex Pattern | 0 | 0% | 31 | 29% | 6.58 ± 1.71 |
| Comet Shape | 0 | 0% | 3 | 3% | 6.47 ± 1.38 |
| Fan Shape | 0 | 0% | 2 | 2% | 5.55 ± 0.92 |
| Random Pattern | 0 | 0% | 1 | 1% | N/A |

TABLE 3

PATTERN DISTRIBUTION IN GROUP 2 SUBGROUPS

| Pattern | Group 2a N = 24 | | Group 2b N = 56 | | Group 2c N = 26 | |
|---|---|---|---|---|---|---|
| Tight Cluster | N = 3 | 13% | N = 5 | 9% | N = 6 | 23% |
| Cluster | N = 6 | 25% | N = 28 | 50% | N = 8 | 31% |
| Open Cluster | N = 0 | 0% | N = 0 | 0% | N = 1 | 4% |
| Cigar | N = 2 | 8% | N = 4 | 7% | N = 2 | 2% |
| Fat Cigar | N = 0 | 0% | N = 3 | 5% | N = 0 | 0% |
| Complex | N = 11 | 46% | N = 13 | 23% | N = 8 | 31% |
| Comet | N = 1 | 4% | N = 1 | 2% | N = 1 | 4% |
| Fan | N = 1 | 4% | N = 1 | 2% | N = 0 | 0% |
| Random | N = 0 | 0% | N = 1 | 2% | N = 0 | 0% |

TABLE 4

POINCARÉ PLOT PATTERNS AND CORRELATION DIMENSION IN HEART FAILURE GROUP

| Pattern | N.Y.H.A. 1 N = 6 | N.Y.H.A. 2 N = 10 | N.Y.H.A. 3 N = 3 | N.Y.H.A. 4 N = 5 |
|---|---|---|---|---|
| Tight Cluster | 1 | 3 | 0 | 0 |
| Cluster | 3 | 1 | 1 | 0 |
| Open Cluster | 0 | 0 | 0 | 0 |
| Complex | 2 | 3 | 2 | 4 |
| Cigar | 1 | 0 | 0 | 1 |
| Fat Cigar | 0 | 0 | 0 | 0 |
| Comet | 1 | 0 | 0 | 0 |
| Fan | 0 | 0 | 1 | 1 |
| Correlation Dimension ± SD | Mean 7.72 ± 2.14 | Mean 7.37 ± 1.99 | Mean 6.2 ± 0.82 | Mean 5.0 ± 3.04 |

TABLE 5

POINCARÉ PLOT PATTERN IN AGE MATCHED GROUP
(N = 106, MEAN AGE = 65 YEARS, SE = 1 YEAR, SD = 10.5 YEARS)

| Variable | Group 1 | Group 2 |
|---|---|---|
| No. of Patients | 21 | 85 |
| Mean age in years ± SE | 64.43 ± 1.98 | 65.2 ± 1.18 |

| Poincaré Plot Pattern | Group 1 | | Group 2 | |
|---|---|---|---|---|
| | N | % | N | % |
| Tight Cluster 0–30 ms | 3 | 14% | 12 | 14% |
| Cluster 31–80 ms | 17 | 81% | 33 | 39% |
| Open Cluster 81–120 ms | 1 | 5% | 1 | 1% |
| Random Pattern | 0 | 0% | 3 | 4% |
| Cigar Shape | 0 | 0% | 8 | 9% |
| Fat Cigar Shape | 0 | 0% | 3 | 4% |
| Complex Pattern | 0 | 0% | 24 | 26% |
| Comet Shape | 0 | 0% | 2 | 2% |
| Fan Shape | 0 | 0% | 1 | 1% |
| Correlation Dimension Mean ± SE | 8.44 ± 0.28 | | 7.29 ± 0.17 | |

The example illustrates the Poincaré plot and its correlation dimension are closely related. The Poincaré plot pattern reflects the degree of autonomic activity, and the correlation dimension quantifies it. The system is predominantly influenced by the sympathetic nervous system if the correlation dimension is low, i.e. below 8.25. A correlation dimension of 8.25, which was the mean of the healthy group, reflects a balanced neurohumoral mechanism in the normal alert state. A further increase in the correlation dimension can occur in systems dominated by the parasympathetic nervous system, such as in extremely fit individuals or subjects in states of deep relaxation. The correlation dimension of the heart rate variability data discriminates between chaos and noise, and the chaotic time series can be the subject of further analysis by prediction algorithms. It has been shown that in heart failure patients the predominant driving force acting on the cardiac pacemaker is the sympathetic system as evidenced by an increase in plasma catecholamine levels that correlate directly with the severity of the heart failure. The Poincaré plot provides a visual guide to the non-linear processes influencing heart rate variability. The patterns produced by the heart failure group were quite distinctive from the normal control group. This qualitative difference was quantified using the correlation dimension which can be considered to be the fractal dimensionality of the plot. As the correlation dimension varied inversely with the degree of heart failure it is considered that the correlation dimension measures the activity of the sympathetic nervous system in these patients.

SECOND EXAMPLE 12 healthy subjects (7 male, 5 female) aged between 20 to 40 (mean 30.2±7.2 years) were recruited. The subjects were included if they did not smoke, had no cardiovascular conditions and were not taking any medications. They were instructed to have a light breakfast and not consume alcohol or caffeinated beverages for 12 hours prior to a study. All studies were performed with the subjects breathing spontaneously and remaining undisturbed in a quiet, temperature controlled room.

Subjects were rested for 10 minutes prior to data collection. All subjects were in sinus rhythm and were examined in the post absorptive state between 10 am and 5 pm. They were instructed to relax and breathe quietly for all studies. A total of 2000 data points were collected for each study segment and used to generate the Poincaré plot. Accordingly, data epochs varied from 20 to 40 minutes.

Four autonomic perturbation protocols were performed for each study as follows:

1. Baseline study. All baseline studies were conducted on subjects in the post absorptive state after resting quietly for 10 minutes in the supine position in a quiet temperature controlled room.
2. 70° head up tilt. All subjects were tilted to 70° on a tilt table for the duration of the study. Heart rate variability data was collected after allowing 5 minutes for the heart rate to stabilise. Tilting a subject in this manner is known to increase sympathetic activity and reduce parasympathetic activity.
3. Atropine infusion. 1.2 mg atropine sulphate was added to 50 ml of 5% IV dextrose and infused at a rate of 50 ml/min (0.12 mg/min) for 5 minutes and then at a rate of 1 ml/min (0.024 mg/min) until the completion of the study. This infusion is known to decrease parasympathetic activity in a subject.
4. Transdermal scopolamine. A transdermal scopolamine (Ciba-Geigy; hyoscine 1.5 mg) patch was applied to an undamaged hair-free area of skin behind the ear one week after the atropine infusion study on the evening prior to the study. The patch remained in situ for the duration of the study. This application is known to enhance parasympathetic activity.

R-R intervals were collected using an Amlab™ data acquisition workstation, provided by Associative Measurements Pty. Ltd., Sydney, Australia, using a program designed to trigger on the R-wave leading edge. The system was calibrated to return a reliable R-R interval to better than 1 msec accuracy.

Poincaré plots were constructed using the raw R-R data and analysed using standard statistical methods for the analysis of heart rate variability (HRV) to quantify the plots using conventional statistical measures. The methods included plotting of R-R interval tachograms and respective R-R and ΔR-R histograms and standard deviations. Most of the time domain and frequency domain techniques in use for HRV studies provide an accurate and common measure of cardiac autonomic tone, as discussed in "Heart rate variability: A measure of cardiac autonomic tone", by Stein et al., American Heart Journal 1994, Vol. 127, pages 1376–1381.

Frequency domain indices were also calculated using carefully filtered data sets and these were compared to the time domain indices. Because the data epochs ranged from 20 to 40 minutes the frequency range measured ranged from the very low frequency (VLF) 0.005 Hz (3 minute cycles) to high frequency (HF) 0.4 Hz (2.5 second cycles). The power spectrum was classified into three bands: VLF(0.005–0.07 Hz,), MF(0.07–0.15 Hz) and HF(0.15–0.4 Hz). VLF and MF were also grouped into LF(0.005–0.15 Hz) to aid in the comparison with time domain variables.

Artefact and occasional ectopic beats occurred in almost all heart rate variability studies. To reduce the effect of such "noise",filters can be used to remove selected portions of the R-R interval data (time series). A conventional technique filters the R-R time series by replacing ectopic beats with an interpolative splined R-R interval. This technique is effective in removing the most obvious ectopic beats from the data but may not remove all "outlying" points. The Poincaré plot was used to check the adequacy of the conventional filtering technique which is applied to the raw R-R data until the filtered Poincaré plot represents as close as possible the original plot with all the outlying data points removed.

The Poincaré plot provides summary information as well as information about the instantaneous beat-to-beat behaviour of the heart. When the basic rhythm is very regular with little interbeat variability, points representing the R-R interval are spread closely along the line of identity 60, which is the diagonal line 60 at an angle of 45° to both axes. Any points below this indicate a shorter R-R interval relative to the preceding R-R interval. Similarly, any points above the diagonal line indicate an R-R interval longer than the preceding R-R interval.

Consequent to this it becomes apparent that the degree of heart rate variability is graphically displayed as a pattern of points which lends itself to analysis more readily than simple summary statistical measures such as the standard deviation of R-R intervals applied to normally distributed data. It also provides a visual display of both the overall and beat-to-beat variability. The histograms 56 and 58 of R-R and ΔR-R data associated with the Poincaré plot can be quantified by the analysis of variance of the respective data. The standard deviation (SD) of the R-R interval histogram 56 relates to the variance of the data distributed along the diagonal line 60 of the Poincaré plot projected onto either the x or y axes. The standard deviation of the difference between R-R intervals (ΔR-R) relates to the variance of the distribution of data points perpendicular to the diagonal line 60, and is considered an indicator of rapid heart rate fluctuations due to the modulation of vagal tone, as discussed in "Components of heart rate variability: What they really mean and what we really measure", by Malik M. and Camm A. J. , Am J Cardiol, 1993;72:821–2. These aspects of the Poincaré plot are illustrated in FIG. 12. Therefore, to summarise the long axis 50 and the short axis 52 of the Poincaré plot 54 relate to the standard deviation of the R-R interval histogram 56 and the ΔR-R interval histogram 58, respectively. The ΔR-R histogram 58 is a measure of spread around the line of identity 60. A measure which quantifies the relationship between the two measures of heart rate variability is the "aspect ratio" which is the ratio of SD R-R to SD ΔR-R intervals. This allows the classification of the various Poincaré plot patterns to be based on objective measures of variance, and normality or otherwise of data distribution.

Heart rate variability data histograms are accepted as stationary if the mean and variance of R-R intervals remained constant throughout the study. Paired Student's t test and repeated measures of Analysis of Variance (ANOVA) and the non-parametric Friedmans RM ANOVA were used where appropriate to evaluate the differences in measures of heart rate variability in the subjects between the four protocols. Non-parametric, between groups analysis (Kruskal-Wallis ANOVA) was also used to assess the significance of the various measures of heart rate variability between the four protocols. All data are expressed as means (±SD). A two tailed p value <0.05 was considered significant. Linear regression analysis was used to assess the relation of frequency and time domain variables.

The results obtained are shown below in Table 6 and discussed below for each protocol.

In the frequency domain, although the VLF, LF and HF all decreased in power with tilting, only LF($t=3.2$, $p=0.009$) and HF($t=4.1$, $p=0.002$) achieved statistical significance.

3. Heart rate variability during atropine sulphate infusion

All subjects had a significant increase in heart rate from 60 to 85 bpm ($t=10.4$, $p<0.001$). Most subjects (92%) displayed cigar pattern characterised by a short length (SD R-R<30 msec) and a narrow width (SD ΔR-R<10 reset) which was significantly different to baseline measurements ($t=5.5$ and $6.4$, $p=<0.001$). The difference in coefficient of variation of R-R and ΔR-R intervals was also highly statistically significant ($t=4.4$ and $7.3$, $p<0.002$).

All frequency domain variables were significantly reduced ($p<0.004$).

4. Heart rate variability during transdermal scopolamine (hyoscine 1.5 mg)

Although heart rate decreased from baseline in all subjects from 60 50 bpm, this failed to achieve significance. Eight subjects produced an open cluster Poincaré pattern and four a cluster pattern. Whilst the SD of R-R intervals increased significantly ($p=0.2$) from 80 to 100, the increase in coefficient of variation of R-R intervals from 9.1 to 9.4

TABLE 6

| Heart Rate Variability | Baseline (mean ± SD) | Head up tilt (mean ± SD) | Atropine (mean ± SD) | Scopolamine (mean ± SD) |
|---|---|---|---|---|
| rate | 60.5 ± 9.5 | 80.9 ± 12.4** | 83.4 ± 9.8** | 58.0 ± 7.2 (NS) |
| SD RR | 82.5 ± 26.9 | 60.3 ± 21.9* | 36.2 ± 14.0** | 98.0 ± 28.5* |
| coeff RR | 8.1 ± 2.2 | 7.9 ± 2.2 (NS) | 5.0 ± 1.8** | 9.4 ± 2.5 (NS) |
| SD ΔRR | 63.7 ± 28.8 | 26.1 ± 18.0** | 8.5 ± 3.9** | 91.8 ± 40.1** |
| coeff ΔRR | 6.2 ± 2.3 | 3.3 ± 1.7** | 1.1 ± 0.4** | 8.7 ± 3.2** |
| aspect ratio | 1.4 ± 0.4 | 2.7 ± 0.9** | 4.7 ± 1.4** | 1.1 ± 0.2* |
| r_MSSD | 63.7 ± 28.8 | 26.1 ± 18.0** | 8.5 ± 3.9** | 91.8 ± 40.1** |
| pNN50 | 36.6 ± 21.0 | 9.0 ± 14.6** | 0.6 ± 1.5** | 51.0 ± 16.7** |
| VLF | 891 ± 736 | 577 ± 503* | 120 ± 72** | 975 ± 580 (NS) |
| MF | 472 ± 376 | 265 ± 209* | 22 ± 21** | 680 ± 530* |
| LF = VLF + MF | 1363 ± 973 | 842 ± 636** | 142 ± 87** | 1655 ± 936 (NS) |
| HF | 598 ± 556 | 129 ± 169** | 9.8 ± 11.6** | 1260 ± 11331** |
| LF/HF (ratio) | 2.9 ± 1.1 | 12.4 ± 8.2** | 21.7 ± 11.3** | 1.8 ± 0.8** |

Legend:
NS=not significant; *$p<0.05$; **$p<0.005$
mean±SD (standard deviation); VLF(0.005–0.07 Hz);
MF(0.07–0.15 Hz); LF=VLF+MF; HF(0.15–0.4 Hz)

1. Heart rate variability in baseline

All subjects displayed a Gaussian (normal) clustering of data (R-R) points, characterised by the SD R-R intervals of 55 to 142 msec (mean 82±27 msec) and SD ΔR-R intervals of 27 to 123 msec (mean 64±29 reset). All subjects produced either a cluster (60%) or open cluster (40%) Poincaré plot pattern type. The aspect ratio ranged from 0.95 to 2.2.

2. Heart rate variability during 70° head up tilt

All subjects displayed a reduction in variance of both R-R and delta R-R intervals as compared to the baseline study. The Poincaré pattern reflected this change with a reduction in length and breadth of the plot, most subjects (75%) produced a fat cigar pattern. Of the remainder, two produced an open cluster and one a cluster pattern, where they had all produced an open cluster pattern in the baseline study. Heart rate increased significantly ($t=7.7$, $p<0.001$) from 60.4±9.5 to 80.9±12.4 beats per minute (bpm) during tiring. The SD of R-R intervals was significantly different to the baseline value ($t=5.1$, $p=0.004$), but the coefficient of variation of R-R intervals was not. However the difference in SD of ΔR-R intervals and coefficient of variation of ΔR-R intervals between baseline and tilt were both highly significant ($p<0.001$).

failed to achieve significance. This contrasted to the measure of width of the Poincaré plot, the SD of ΔR-R intervals which increased significantly ($p<0.003$). with the transdermal scopolamine and was reflected in a significant increase in the coefficient of variation of ΔR-R intervals ($p<0.004$).

Analysis of data in the frequency domain reflected the time domain results. The LF power increased, but did not reach statistical significance whereas the HF power increased significantly ($p=0.003$) with the application of the scopolamine patch.

Poincaré plots generated by one of the subjects, a 39 year old female, for the various phases of the study is shown in FIGS. 13 to 17. The plot 100 generated during the baseline study exhibits a "cluster" pattern, and the SD of R-R and ΔR-R intervals was 71 and 50 msec, respectively. The plot 102 generated during the head up tilt is a "far cigar", and the SD of R-R and ΔR-R intervals was 50 and 11 msec, respectively. The plot 104 generated during atropine infusion is a "cigar" or "torpedo", and the SD of R-R and ΔR-R intervals was 34 and 9 msec, respectively. Finally, the plot 106 generated during the transdermal scopolamine application has a "open cluster" pattern, and the SD of R-R and ΔR-R intervals was 81 and 72 msec, respectively.

The measure of heart rate variability provides a non-invasive mechanism with which to quantify autonomic activity. There are several invasive techniques which can provide some measure of autonomic function. These include microneurographic measurements of sympathetic nervous activity, as discussed in "Clinical and hemodynamic correlates of sympathetic nerve activity in normal humans and patients with heart failure: Evidence from direct microneurographic recordings", by Ferguson D. W., Berg W. J. and Sanders J. S., J Am Coll Cardiol, 1990;16:1125-34, and regional catecholamine "spillover", as discussed in "Noradrenaline release and sympathetic nervous system activity", by Elser M. D. et al., 1985;3:117-29, which has been used to reflect sympathetic activity in particular organs such as the heart. However in the past there have been no reliable non-invasive tests available to allow complete assessment of autonomic function, as discussed in "Comparison of time and frequency domain-based measures of cardiac parasympathetic activity in Holter recordings after myocardial infarction", by Bigger et al., Am J Cardiol, 1989;64:536-8.

The above study demonstrates that the Poincaré plot pattern reflects the conventional time parameters used to quantify autonomic activity in subjects undergoing autonomic perturbation. The "width" 52 of the Poincaré plot, as quantified by the SD of ΔR-R intervals varies directly with the expected perturbation of the autonomic nervous system. The width of the Poincaré plot and the SD of ΔR-R intervals provide a pure measure of parasympathetic activity.

The paper "Comparison of time and frequency domain-based measures of cardiac parasympathetic activity in Holter recordings after myocardial infarction", by Bigger et al., Am J Cardiol, 1989;64:536-8, shows a strong correlation between the power in the high frequency energy of the normal R-R interval power spectrum and the root mean squared successive difference (r-MSSD) of normal R-R intervals. The standard deviation of the successive differences between R-R intervals as discussed in "Circadian variation of heart rate variability", by Malpas S. C. and Purdie G. L., Cardiovasc Res, 1990;24:210-3 and r-MSSD are equivalent to the SD of ΔR-R interval measure which we have used to quantify the short axis of the Poincaré plot. Therefore the Poincaré plot pattern effectively displays the interaction between the R-R and ΔR-R interval data.

The Second Example also shows a strong correlation between frequency and time domain measures used to quantify heart rate variability. The LF power (VLF+MF) is reflected in the "length" of the Poincaré plot and the HF power in the "width". The frequency domain parameters provide supportive evidence. LF power (0.005-0.015 Hz) correlated with variance of R-R intervals (r=0.94, p<0.001) and HF(0.15-0.4 Hz) correlated with variance of ΔR-R intervals (r=0.97, p<0.001). The LF/HF ratio in the frequency domain correlated (r=0.96, p<0.001) with the aspect ratio (SD R-R/SD ΔR-R) of the time domain.

The low frequency (LF) component of spectral energy has been proposed as reflecting sympathetic and parasympathetic activity; and the high frequency (HF) as representing pure parasympathetic activity, as discussed in "Assessment of autonomic function in humans by heart rate spectral analysis", by Pomeranz B. et al., Am J Physiol, 1985;248:H151-3. The ratio of LF to HF (LF/HF) is considered to be an indicator of sympatho-vagal balance, as discussed in "Power spectral analysis of heart rate and arterial pressure variabilities as a marker of sympatho-vagal interaction in man and dog", by Pagani M. et al., Circ Res, 1986;59:178-93.

It is significant that in contrast to most studies of heart rate variability which rely on data collected during prolonged ambulatory Holter monitoring, the patients were resting quietly with data collected over a relatively short time-frame of 20 to 40 minutes. This is the likely explanation for the fact that the healthy subjects did not display Poincaré plot patterns with the characteristic "comet" and "stem" shape seen in the patterns of healthy subjects in the study discussed in "Patterns of beat-to-beat heart rate variability in advanced heart failure", by Woo M. A. et al., Am Heart J, 1992;123:704-10, which employed 24 hour ambulatory monitoring. The small "head" of their "comet" pattern was probably the result of increased sympathetic activity resulting in an increase in absolute heart rate and associated reduction in heart rate variability.

Analysis of HRV based on short term analysis provides a sensitive, non-invasive measurement of autonomic input into the heart. HRV can be measured in the time or frequency domain, and frequency domain variables have been shown to correlate very highly (r>0.97) with time domain variables. Thus time domain indices used to quantify the Poincaré plot are excellent surrogates for frequency domain variables which greatly simplifies studies of HRV.

The Poincaré plot in conjunction with conventional heart rate variability analysis tools provides an important method of displaying and quantifying heart rate variability date in a clinical setting. The apparatus and method of the present invention therefore provides a cheap and reliable method of assessing heart failure, and measuring and quantifying activity of the autonomic nervous system, in a non-invasive manner within a relatively short period of time.

```
    REM PK's beat to beat period data collector.
    SCREEN 2
    CLS
    INPUT "Name of data file..remember only 5 letters.."; name$
10 CLS
    DIM A(5000), B(5000)
    COUNT = 0
    TOT = 0
    test = 0
    num = 0
    total = 0
    CLS
    n$ = name$ + "_5.dat"
    CLS
15  LOCATE 10, 30: PRINT "Current period:"
    LOCATE 20, 30: PRINT "F2 to Save ...press CNTRL-BRK to finish"

25 ON KEY(2) GOSUB 400
27 KEY(2) ON
30 XB = &H378
40 outp = XB: INPO = XB + 1: CPO = XB + 2      'Port ddresses
100 OUT CPO, 1
    T$ = TIME$
    TIMER ON: t1 = TIMER
DO
120 test = (INP(INPO) AND 8): ' PRINT test
130 COUNT = COUNT + 1: IF test <> 8 THEN 120
310 TOT = COUNT: COUNT = 0: LOCATE 10, 46: PRINT TOT
320 A(num) = TOT
330 num = num + 1
331 PRINT "number of beats:"; num
335 FOR x = 1 TO 100: NEXT x
LOOP WHILE num < 2200
400 TIMER OFF: BEEP
t2 = TIMER
Tfinish$ = TIME$
OPEN n$ FOR OUTPUT AS #1
401 time = t2 - t1
402 FOR x = 0 TO num
403 total = total + A(x)
404 NEXT x
405 ratio = time / total
d$ = DATE$
406 WRITE #1, num, ratio, total, time, d$, T$, Tfinish$
410 FOR x = 0 TO num
426 deltaT = ratio * 1000 * A(x)
427 B(x) = deltaT
431 WRITE #1, B(x)
432 NEXT x
450 CLOSE #1
455 rate = num / (time / 60)
460 PRINT "ratio:"; ratio
470 PRINT "total time taken:"; time; "seconds"
475 PRINT "average heart rate:"; rate; "beats per minute"
PRINT "date:"; d$
600 END
```

```
    xb = &H3BC
    DIM A(5000)
    SCREEN 9
    VIEW (150, 100)-(350, 220)
 5  WINDOW (800, 800)-(2000, 2000)
    INPUT "Name of data file"; name$
    begin: CLS
    outp = xb: INPO = xb + 1: cpo = xb + 2
    PRINT "RETURN MAP R-R INTERVAL versus R-R n-1"
10  VIEW PRINT 17 TO 20
    num = 0
    name$ = name$ + ".dat"
    ON KEY(2) GOSUB finish: ON KEY(7) GOSUB finall: ON KEY(4) GOSUB begin
    KEY(2) ON: KEY(7) ON: KEY(4) ON
15  OUT cpo, 1
    Tstart$ = TIME$
    TIMER ON
    t1 = TIMER
    nloop:
20  test = INP(INPO)
    1 IF (test AND 128) = 128 THEN GOTO nloop
    OUT cpo, 0: OUT cpo, 1
    OUT outp, 14
    NIBBLE1 = (INP(INPO) AND 120) / 8
25  OUT outp, 0
    OUT outp, 10
    NIBBLE2 = (INP(INPO) AND 120) * 2
    OUT outp, 0: OUT outp, 22
    NIBBLE3 = (INP(INPO) AND 120) / 8
30  OUT outp, 0
    OUT outp, 18
    NIBBLE4 = (INP(INPO) AND 120) * 2
    tot = (NIBBLE1 + NIBBLE2) + 256 * (NIBBLE3 + NIBBLE4)
    IF tot = 0 THEN GOTO nloop
35  'IF ((tot < 2900) OR (tot > 14300)) THEN GOTO nloop ELSE GOSUB plot plot:
    num = num + 1
    IF num > 2200 THEN GOTO finish
40  A(num) = (tot / 7812.5) * 500
    total = total + tot
    PSET (A(num), A(num - 1))
    VIEW PRINT 19 TO 20: PRINT "period is......."; (tot / 7812.5) * 500;
    " milliseconds"
45  VIEW PRINT 20 TO 21: PRINT "rate is........."; INT(434375! / tot); * 2;
    " beats per minute"
    VIEW PRINT 21 TO 22: PRINT "number of beats."; num
    VIEW PRINT 22 TO 23: PRINT "F2 to Save & Finish, F4 to Restart, F7 to
    Abort"
50  GOTO nloop finish:
    TIMER OFF
    t2 = TIMER
55  time = t2 - t1
    KEY(2) OFF: KEY(7) OFF: KEY(4) OFF
```

```
    OPEN name$ FOR OUTPUT AS #1
    Tfinish$ = TIME$
    d$ = DATE$
    WRITE #1, num, .0003, total, time, d$, Tstart$, Tfinish$
5   FOR x = 0 TO num
    WRITE #1, A(x)
    NEXT x
    CLOSE #1
    CLS 2
10  STOP: SYSTEM
    finall: SYSTEM
```

```
              CLS
     SCREEN 9
     PRINT "CARDIAC DYNAMICS...Poincare plot"
     s = 2: REM screensize
 5   CLS
     'PRINT "CARDIAC DYNAMICS....Poincare plot"
     s = s * 1000
     :
     VIEW (1, 14)-(530, 330), , 15
10   WINDOW (0, 0)-(s, s)
     LOCATE 2, 1
     INPUT "name of data file:NO EXTENSION"; name$
     name$ = name$ + ".dat"
     OPEN name$ FOR INPUT AS #1
15   INPUT #1, num, ratio, total, time d$, t$, Tfinish$
     DIM A(num)
     FOR x = 0 TO num - 10
     INPUT #1, A(x)
     NEXT x
20   CLOSE #1
     PRINT "total number of beats:"; num; "beats"
     PRINT "total time taken: ";
     PRINT USING "###"; time / 60;
     PRINT " minutes"
25   PRINT "average heart rate: ";
     PRINT USING "###"; num / (time / 60);
     PRINT " beats per minute"
     average = (time * 1000) / num
     PRINT "average R-R interval: ";
30   PRINT USING "###"; average;
     PRINT " milliseconds"
     PRINT "date:"; d$
     :
     FOR d = 4 TO num - 10
35   x = A(d)
     y = A(d - 1)
     PSET (x, y)
     NEXT d
     :
40   'LINE (1000, 0)-(1000, 1000)
     sc = s
     stepsize = (sc / 40) * 5
     LOCATE 24, 1: PRINT "0 ms",
     :
45   FOR x = 9 TO 60 STEP 8
     c = c + 1
     P = c * stepsize
     LOCATE 24, x
     PRINT USING "####"; P;
50   NEXT x
     END
```

I claim:

1. A method of measuring activity of the autonomic nervous system of a patient comprising:
   obtaining ECG signals from said patient whilst said patient is at rest;
   measuring the R-R intervals for adjacent PQRS portions of said signals;
   generating a Poincaré plot from said R-R intervals; and
   determining a level of parasympathetic activity for said patient from the width of said plot about a line perpendicular to the line of identity of said plot.

2. A method as in claim 1, including determining whether the level of parasympathetic activity of the patient represented by the plot corresponds to a level of heart failure.

3. A method as in claim 1, wherein said ECG signals are obtained for a period of less than on hour.

4. A method of measuring activity of the autonomic nervous system of a patient comprising:
   obtaining ECG signals from said patient whilst said patient is at rest;
   measuring the R-R intervals for adjacent PQRS portions of said signals;
   generating a Poincaré plot from said R-R intervals;
   calculating a correlation dimension corresponding to said Poincaré plot, and
   determining a level of sympathetic activity of said patient on the basis of said correlation dimension as a measure of the autonomic nervous system of said patient.

5. A method of measuring activity of the autonomic nervous system of a patient comprising:
   obtaining ECG signals from said patient whilst said patient is at rest;
   measuring the R-R intervals for adjacent PQRS portions of said signals;
   generating a Poincaré plot from said R-R intervals; and
   determining a level of parasympathetic activity for said patient from the width of said plot about a line perpendicular to the line of identity of said plot as a measure of activity of the autonomic nervous system of said patient.

6. A method of determining a level of heart failure in a patient comprising:
   obtaining ECG signals from said patient whilst said patient is at rest;
   measuring the R-R intervals for adjacent PQRS portions of said signals;
   generating and displaying a Poincaré plot of said R-R intervals; and
   determining a level of parasympathetic activity for said patient from the width of said plot about a line perpendicular to the line of identity of said plot, and determining a level of heart failure for said patient if said level of parasympathetic activity is below a predetermined level.

7. A method as in claim 6, wherein said ECG signals are obtained for a period less than one hour.

8. A method as in claim 6, including calculating a correlation dimension corresponding to said Poincaré plot, and if said correlation dimension lies outside a predetermined range the patient has a level of autonomic activity corresponding to a level of heart failure.

9. A method of determining a level of heart failure in a patient comprising:
   obtaining ECG signals from said patient whilst said patient is at rest;
   measuring the R-R intervals for adjacent PQRS portions of said signals;
   generating and displaying a Poincaré plot of said R-R intervals;
   determining a level of autonomic activity from said Poincaré plot which corresponds to a level of heart failure;
   determining a level of parasympathetic activity for said patient from the width of said plot about a line perpendicular to the line of identity of said plot, and
   determining a level of heart failure for said patient if said level is below a predetermined level.

10. A method of quantifying a degree of heart failure in a patient comprising:
    obtaining ECG signals from said patient whilst said patient is at rest;
    measuring the R-R intervals for adjacent PQRS portions of said signals;
    generating and displaying a Poincaré plot of said R-R intervals;
    determining a level of parasympathetic activity for said patient from the width of said plot about a line perpendicular to the line of identity of said plot;
    determining the standard deviation of $\Delta$R-R intervals; and
    quantifying a degree of heart failure of said patient on the basis of said width and said standard deviation.

11. An apparatus for measuring activity of the autonomic nervous system of a patient, comprising:
    means for obtaining ECG signals from said patient whilst each patient is at rest;
    means for measuring the R-R intervals for adjacent PQRS portions of said signals;
    means for generating a Poincaré plot from said R-R intervals; and
    means for determining a level of parasympathetic activity for said patient from the width of said plot about a line perpendicular to the line of identity of said plot.

12. An apparatus as in claim 11, wherein said means for obtaining obtains said ECG signals for a period less than one hour.

13. An apparatus for measuring activity of the autonomic nervous system of a patient, comprising:
    means for obtaining ECG signals from said patient whilst said patient is at rest;
    means for measuring the R-R intervals for adjacent PQRS portions of said signals;
    means for generating a Poincaré plot from said R-R intervals; and
    means for determining the level of autonomic activity of the patient represented by the plot;
    means for calculating a correlation dimension corresponding to said Poincaré plot; and
    means for determining a level of sympathetic activity of said patient on the basis of said correlation dimension.

14. An apparatus for measuring activity of the autonomic nervous system of a patient, comprising:
    means for obtaining ECG signals from said patient whilst said patient is at rest;
    means for measuring the R-R intervals for adjacent PQRS portions of said signals;
    means for generating a Poincaré plot from said R-R intervals; and
    means for determining the level of autonomic activity of the patient represented by the plot; and means for determining a level of parasympathetic activity for said patient from the width of said plot about a line perpendicular to the line of identity of said plot.

15. An apparatus for determining a level of heart failure in a patient comprising:

means for obtaining ECG signals from said patient whilst said patient is at rest;

means for measuring the R-R intervals for adjacent PQRS portions of said signals;

means for generating and displaying a Poincaré plot of said R-R intervals; and means for determining a level of parasympathetic activity for said patient from the width of said plot about a line perpendicular to the line of identity of said plot, and means for determining a level of heart failure in said patient when said level of parasympathetic activity is below a predetermined level.

16. An apparatus as in claim 15, wherein said means for obtaining obtains said EGG signals for a period less than one hour.

17. An apparatus as in claim 15, including:

means for calculating a correlation dimension corresponding to said Poincaré plot, and means for determining the patient has a level of autonomic activity corresponding to a level of heart failure when said correlation dimension lies outside a predetermined range.

18. An apparatus for determining a level of heart failure in a patient comprising:

means for obtaining ECG signals from said patient whilst said patient is at rest;

means for measuring the R-R intervals for adjacent PQRS portions of said signals;

means for generating and displaying a Poincaré plot of said R-R intervals from which a level of autonomic activity corresponding to a level of heart failure can be determined;

means for determining a level of parasympathetic activity for said patient from the width of said plot about a line perpendicular to the line of identity of said plot, and means for determining a level of heart failure in said patient when said level of parasympathetic activity is below a predetermined level.

19. An apparatus for quantifying a degree of heart failure in a patient comprising:

means for obtaining ECG signals from said patient whilst said patient is at rest;

means for measuring the R-R intervals for adjacent PQRS portions of said signals;

means for generating and displaying a Poincaré plot of said R-R intervals from which heart failure can be determined;

means for determining a level of parasympathetic activity for said patient from the width of said plot about a line perpendicular to the line of identity of said plot;

means for determining the standard deviation of $\Delta$R-R intervals; and means for quantifying a degree of heart failure of said patient on the basis of said width and said standard deviation.

* * * * *